US011456082B2

(12) United States Patent
Ito et al.

(10) Patent No.: US 11,456,082 B2
(45) Date of Patent: Sep. 27, 2022

(54) PATIENT ENGAGEMENT COMMUNICATIVE STRATEGY RECOMMENDATION

(71) Applicant: International Business Machines Corporation, Armonk, NY (US)

(72) Inventors: Marcia Ito, Sao Paulo (BR); Livy Maria Real Coelho, São Paulo (BR); Fabio Rezende de Souza, Santo Andre (BR)

(73) Assignee: International Business Machines Corporation, Armonk, NY (US)

( * ) Notice: Subject to any disclaimer, the term of this patent is extended or adjusted under 35 U.S.C. 154(b) by 645 days.

(21) Appl. No.: 16/026,583

(22) Filed: Jul. 3, 2018

(65) Prior Publication Data

US 2020/0013516 A1    Jan. 9, 2020

(51) Int. Cl.
*G16H 80/00* (2018.01)
*G16H 70/20* (2018.01)
(Continued)

(52) U.S. Cl.
CPC .............. *G16H 80/00* (2018.01); *G06F 16/35* (2019.01); *G06F 40/30* (2020.01); *G06N 5/022* (2013.01);
(Continued)

(58) Field of Classification Search
CPC ........ G16H 80/00; G16H 10/60; G16H 70/20; G06F 40/30; G06Q 50/20–26
See application file for complete search history.

(56) References Cited

U.S. PATENT DOCUMENTS 8,214,224 B2   7/2012  Rao et al.
8,721,543 B2   5/2014  Saffarian
(Continued)

FOREIGN PATENT DOCUMENTS

WO    WO 2007005184 A2    1/2007

OTHER PUBLICATIONS

Srivastava, Measuring the effectiveness of the communication strategy by using Brand Score Technique—a practitioner Study, 20(3) Measuring Business Excellence 26-41 (Nov. 3, 2016) (Year: 2016).*

(Continued)

*Primary Examiner* — Evangeline Barr
*Assistant Examiner* — Jordan L Jackson
(74) *Attorney, Agent, or Firm* — Scully, Scott, Murphy & Presser, P.C.; Joseph Petrokaitis

(57) ABSTRACT

Methods and systems for outputting an engagement communicative strategy are described. In an example, a processor may train a communicative model using a patient authored text corpus. The processor may generate at least one patient profile based on the patient authored text corpus and patient authored health data. The processor may construct a knowledge based system based on the communicative model and the at least one patient profile. The processor may input a patient profile of the entity, an engagement degree, and an engagement score to the knowledge based system. The processor may execute the knowledge based system to determine the engagement communicative strategy, and may output the engagement communicative strategy. The engagement communicative strategy may specify a communication scheme to communicate with the entity.

20 Claims, 12 Drawing Sheets

(51) Int. Cl.
  *G16H 10/60*  (2018.01)
  *G06N 5/02*  (2006.01)
  *G06N 20/00*  (2019.01)
  *G06F 40/30*  (2020.01)
  *G06F 16/35*  (2019.01)

(52) U.S. Cl.
  CPC .............. *G06N 20/00* (2019.01); *G16H 10/60* (2018.01); *G16H 70/20* (2018.01)

(56) References Cited

U.S. PATENT DOCUMENTS

| | | | |
|---|---|---|---|
| 8,949,131 | B2 | 2/2015 | Abella et al. |
| 10,127,214 | B2* | 11/2018 | Munro .................. G06F 16/367 |
| 2005/0108051 | A1 | 5/2005 | Weinstein |
| 2011/0077973 | A1 | 3/2011 | Breitenstein et al. |
| 2013/0304508 | A1 | 11/2013 | Shah |
| 2015/0187037 | A1 | 7/2015 | Subramanian et al. |
| 2015/0189086 | A1 | 7/2015 | Romano et al. |
| 2015/0216413 | A1* | 8/2015 | Soyao .................... G16H 10/60 709/204 |
| 2015/0262499 | A1* | 9/2015 | Wicka ................ G06Q 30/0279 705/14.27 |
| 2016/0343265 | A1 | 11/2016 | Deng et al. |
| 2017/0011190 | A1* | 1/2017 | Joao ........................ G16H 20/40 |
| 2017/0177801 | A1* | 6/2017 | Ryan ....................... G16H 50/20 |
| 2017/0220964 | A1* | 8/2017 | Datta Ray ............... H04L 63/20 |
| 2017/0228520 | A1* | 8/2017 | Kidd ........................ G16H 20/13 |
| 2017/0286616 | A1 | 10/2017 | Sharad et al. |
| 2017/0300637 | A1 | 10/2017 | Kumar et al. |

OTHER PUBLICATIONS

Friedman et al., Natural language processing: State of the art and prospects for significant progress, a workshop sponsored by the National Library of Medicine, 46 J of Biomedical Informatics 765-773 (Jun. 25, 2013) (Year: 2013).*

Kreuterand Wray, Tailed and Targest Health communication: Strategies for Enhancing Information Relevance, 27(Supp 3) Am J Health Behavior S227-S232 (Year: 2003).*

James Pustejovsky and Amber Stubbs, Natural Language Annotation for Machine Learning, O'Reilly (Oct. 2012) (Year: 2012).*

Seth M. Noar, PhD., A Health Educator's Guide to Theories of Health Behavior, 24(1) Int'l. Quarterly of Community Health Education 75-92 (Year: 2005).*

Yang et al., Semantic Inference on Clinical Documents: Combining Machine Learning Algorithms With an Inference Engine for Effective Clinical Diagnosis and Treatment, 5 IEEE Access 3529-3546 (Mar. 28, 2017) (Year: 2017).*

Anonymous, "Method and System for Maximizing User's Engagement with a Patient", IP>com Prior Art Database Technical Disclosure, IPCOM000250399D, Jul. 11, 2017, cover page and p. 1.

Sairamesh et al., "Early Warning and Risk Estimation methods based on Unstructured Text in Electronic Medical Records to Improve Adherence and Care", AMIA Annual Symposium Proceedings, Nov. 14, 2009, pp. 553-557.

Mayfield et al., "Automating annotation of information-giving for analysis of clinical conversation", Journal of the American Medical Informatics Association, Feb. 2014, 21(e1), pp. e122-e128.

Wallace et al., "Automatically Annotating Topics in Transcripts of Patient-Provider Interactions via Machine Learning", Medical Decision Making, May 2014, 34(4), Published online Nov. 2, 20137, pp. 503-512.

Howes et al., "Predicting Adherence to Treatment for Schizophrenia from Dialogue Transcripts", Proceedings of the 13th Annual Meeting of the Special Interest Group on Discourse and Dialogue (SIGDIAL), Seoul, South Korea, Jul. 5-6, 2012, pp. 79-83.

Li et al., "Developmetn of engagement evaluation method and learning mechanism in an engagement enhancing rehabilitation system", Journal Engineering Applications of Artificial Intelligence, vol. 51, May 2016, pp. 182-190.

* cited by examiner

PATIENT ENGAGEMENT COMMUNICATIVE STRATEGY RECOMMENDATION

FIELD

The present application relates generally to computers, and computer applications, and more particularly to computer-implemented methods and systems relating to health informatics systems.

BACKGROUND

In an example, patient engagement refers to a patient that takes an active role as a key player in protecting his or her health, choosing appropriate treatments for episodes of ill health, and managing chronic diseases. In some examples, patients who are engaged tend to use fewer healthcare resources, make better decisions, and may have better health outcomes. In some examples, low patient engagement may result from communication problems between patients and healthcare professionals.

SUMMARY

In some examples, a method for outputting an engagement communicative strategy is generally described. The method may comprise receiving, by a processor, a patient authored text corpus. The method may further comprise receiving, by the processor, patient authored health data. The method may further comprise training, by the processor, a communicative model based on the patient authored text corpus. The method may further comprise generating, by the processor, at least one patient profile based on the patient authored text corpus and the patient authored health data. The method may further comprise constructing, by the processor, a knowledge based system based on the communicative model and the at least one patient profile. The knowledge based system may include an inference engine and a knowledge base. The method may further comprise receiving, by the processor, a request for an engagement communicative strategy associated with an entity. The method may further comprise retrieving, by the processor, a patient profile of the entity from the at least one patient profile. The method may further comprise inputting, by the processor, the patient profile, an engagement degree, and an engagement score to the knowledge based system. The engagement degree may be representative of a level of engagement of the entity in a patient engagement process, and the engagement score may be representative of an effectiveness of a strategy to improve the level of engagement of the entity in the patient engagement process. The method may further comprise executing, by the processor, the knowledge based system to determine the engagement communicative strategy associated with the entity based on the patient profile, the engagement degree, and the engagement score. The method may further comprise outputting, by the processor, the engagement communicative strategy. The engagement communicative strategy may specify a communication scheme to communicate with the entity.

In some examples, a system effective to output an engagement communicative strategy is generally described. The system may comprise a memory configured to store a set of engagement instructions, and a processor configured to be in communication with the memory. The processor may be configured to execute the set of engagement instructions stored in the memory. The processor may be further configured to receive a patient authored text corpus. The processor may be further configured to receive patient authored health data. The processor may be further configured to train a communicative model based on the patient authored text corpus. The processor may be further configured to generate at least one patient profile based on the patient authored text corpus and the patient authored health data. The processor may be further configured to construct a knowledge based system based on the communicative model and the at least one patient profile. The knowledge based system may include an inference engine and a knowledge base. The processor may be further configured to receive a request for an engagement communicative strategy associated with an entity. The processor may be further configured to retrieve a patient profile of the entity from the at least one patient profile. The processor may be further configured to input the patient profile, an engagement degree, and an engagement score to the knowledge based system. The engagement degree is representative of a level of engagement of the entity in a patient engagement process, and the engagement score may be representative of an effectiveness of a strategy to improve the level of engagement of the entity in the patient engagement process. The processor may be further configured to execute the knowledge based system to determine the engagement communicative strategy associated with the entity based on the patient profile, the engagement degree, and the engagement score. The processor may be further configured to output the engagement communicative strategy. The engagement communicative strategy may specify a communication scheme to communicate with the entity.

In some examples, a computer program product for outputting an engagement communicative strategy is generally described. The computer program product may include a computer readable storage medium having program instructions embodied therewith. The program instructions may be executable by a processing element of a device to cause the device to perform one or more methods described herein.

Further features as well as the structure and operation of various embodiments are described in detail below with reference to the accompanying drawings. In the drawings, like reference numbers indicate identical or functionally similar elements.

DETAILED DESCRIPTION

Figure 1:
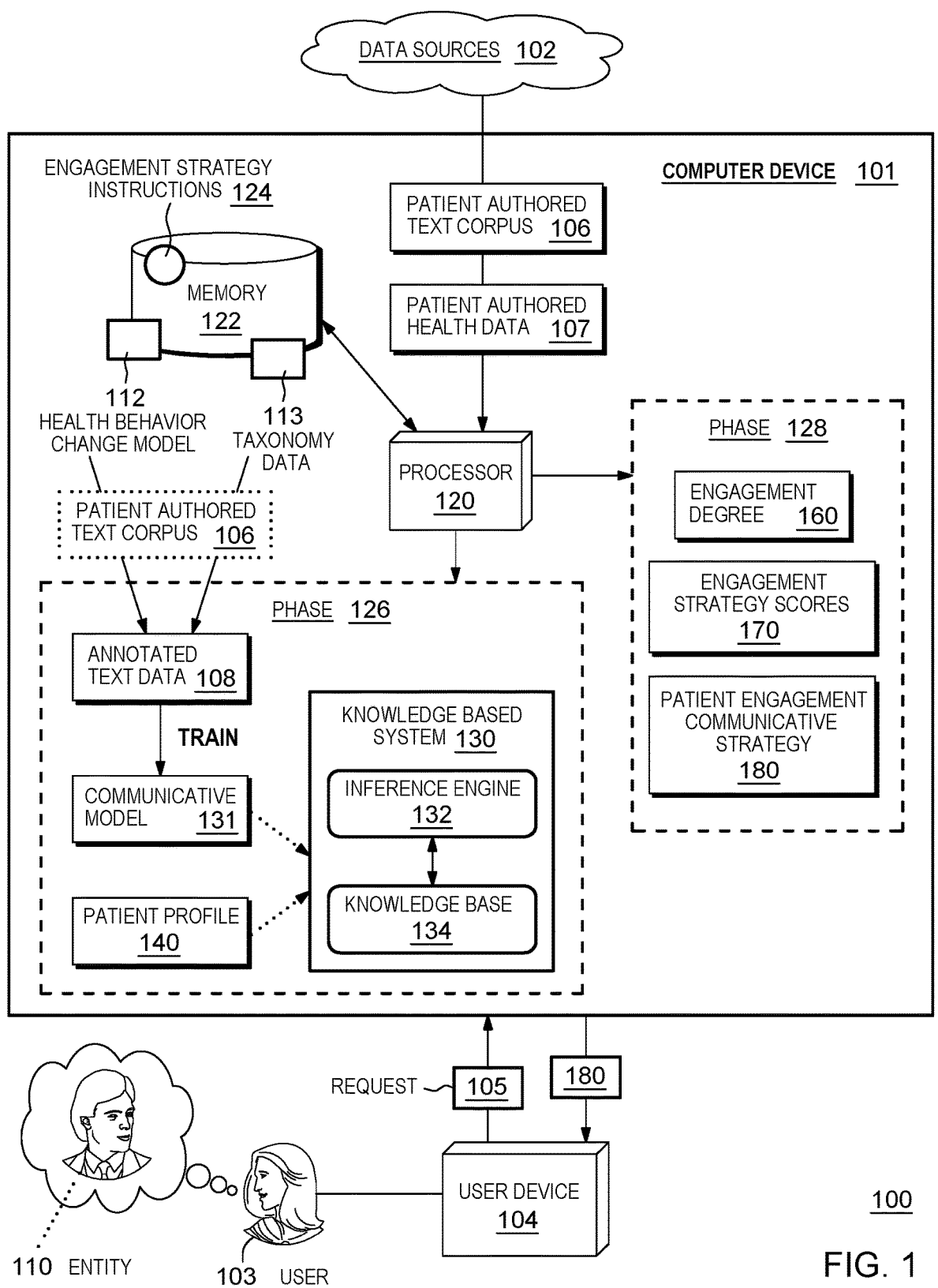
FIG. 1 illustrates an example computer system in one embodiment that can be utilized to implement patient engagement communicative strategy recommendation in one embodiment.

Improvement of patient engagement may ensure the sustainability of health systems and to improve the population health. In some examples, low patient engagement may occur due to problems of health literacy, lack of treatment decision-making and bad self-management of chronic conditions. Problems in communications between patients (or caregivers of the patients) and healthcare professionals may be one of the causes of the low patient engagement. Thus, methods and systems that help the governments, health authorities or healthcare professionals to define the best patient engagement communicative strategy to apply to one or more patients are needed to improve health informatics systems, where the improved health informatics systems may provide improvements to patient engagement. In an example, communication strategies may be defined as the blueprints of how information may be exchanged between a first user and a second user. Thus, a patient engagement communicative strategy determined from a system in accordance with the present disclosure (e.g., system 100 shown in FIG. 1) may improve a health informatics system by recommending communication strategies to improve patient engagement, such as, how to exchange health information between one or more patients and healthcare professionals.

System 100 may be implemented to provide assistance on communications with one or more patients by defining optimal patient engagement communicative strategies. The patient engagement communicative strategy provided by the system 100 may indicate a strategy to improve how to exchange health information between patients and healthcare professionals in order to promote patient engagement. The system 100 may provide a cognitive solution to improve the communication between the patients and the healthcare professionals. The system 100 may combine the knowledge of the health professionals to create an automated system to support the healthcare professionals to effectively communicate with the patient. In an example, healthcare professionals may include psychologists, physicians, nurses, linguists, social workers, and/or other health professionals. The system 100 may provide improvements to health informatics systems by allowing the health informatics systems to perform functions to output communicative strategy in additional to management of patient profiles and healthcare data.

To develop the patient engagement communicative strategy, the system 100 may define a patient profile for each patient from an analysis of data received from different sources, such as annotated dialog corpus, patient generated health data, patient clinical data, and/or other data. The system 100 may further analyze and classify the defined patient profile according to engagement stages chosen from a modeling phase. The system 100 may further determine, or calculate, a patient engagement degree and a score of strategies for patient engagement. The system 100 may further determine a personalized patient engagement communicative strategy based on the patient profile, engagement degree and the score of the engagement strategies. In an example, the system 100 may receive an inquiry from a user (e.g., a healthcare professional), and in response, may develop and/or select an optimal patient engagement communicative strategy based on a context of a patient indicated by the inquiry and a context of the user.

Some example systems may evaluate the patient engagement but fail to propose communicative strategies. Some example systems may propose automatic annotation of dialogs in a clinical context but the annotate dialogs may not be used to evaluate the patient engagement or to propose improvements on communications with the patients. Some example systems may fail to consider patient engagement or a dialog taxonomy to structure and measure various patient data. Some example systems may use dialog analysis to measure patient adherence to treatment, but may fail to offer a communicative strategy to provide suggestions to improve the communication between patient and healthcare professionals, and may fail to apply to generic cases of health treatment or the use of historical patient data to assure a strategic and personalized analysis of the patient dialogue.

FIG. 1 illustrates an example computer system 100 that can be utilized to implement patient engagement communicative strategy recommendation, arranged in accordance with at least some embodiments described herein. In some examples, the system 100 may be a health informatics system implemented by a computer device 101. The system 100 may include a processor 120 and a memory 122 configured to be in communication with each other. The processor 120 may be a central processing unit of the computer device 101. In some examples, the processor 120 may be configured to control operations of the memory 122 and/or other components of the computer device 101. In some examples, the computer device 101 may include additional hardware components, such as programmable logic devices, microcontrollers, memory devices, and/or other hardware components, that may be configured to perform respective tasks of the methods described in the present disclosure. In some examples, the processor 120 may be configured to execute software modules that include instructions to perform each respective task of the methods described in the present disclosure. In some examples, the processor 120 and/or the memory 122 may be parts of resources provided by a cloud computing platform.

The memory 122 may be configured to selectively store instructions executable by the processor 120. For example, in one embodiment, the memory 122 may store a set of engagement strategy instructions 124, where the engagement strategy instructions 124 may include instructions, such as executable code, related to machine learning algorithms, ontology, graph and network algorithms, text inference, linguistic processing algorithms, artificial intelligence, cognitive interactions, and/or other algorithms or techniques, which may implement the system 100. The processor 120 may be configured to execute one or more portions of the engagement strategy instructions 124 in order to facilitate implementation of the system 100. In some examples, the engagement strategy instructions 124 may be packaged as a standalone application that may installed on the computer device 101 such that the engagement strategy instructions 124 may be executed by the processor 120 to implement the system 100. In some examples, the engagement strategy instructions 124 may be integrated into an existing health informatics system in order for the existing health informatics system to perform the methods described in the present disclosure. In some examples, the engagement strategy instructions 124 may be stored in a programmable hardware component that may be embedded as part of the processor 120 and/or the computer device 101.

In some examples, the memory 122 may be further configured to store a plurality of models, such as a health behavior change model 112. In some examples, the memory 122 may be further configured to store taxonomy data 113 associated with a plurality of communicative taxonomies, or taxonomies relating to linguistics, communicative acts, etc.

In an example, the system 100 may be implemented in a plurality of phases—a phase 126 to construct a knowledge based system 130 that may include an inference engine 132 and a knowledge base 134, and a phase 128 to execute the knowledge based system 130 to generate a patient engagement communicative strategy 180 corresponding to an entity 110.

In an example, a user 103 (e.g., a healthcare professional) may use a user device 104 to send a request 105 to the computer device 101. The request 105 may be a request for the patient engagement communicative strategy 180 that corresponds to the entity 110, such as a patient. The computer device 101 may receive the request 105 and may generate the patient engagement communicative strategy 180 corresponding to the entity 110. The computer device 101 may send the patient engagement communicative strategy 180 to the user device 104 to fulfill the request 105.

The processor 120 may be configured to obtain or receive patient authored text corpus 106 from a plurality of data sources 102. The patient authored text corpus 106 may be a structured set of text data that may be processed by the processor 120 using the linguistic processing algorithms that may be among the engagement instructions 124. The patient authored text corpus 106 may be obtained or received from data sources such as social media, healthcare social media, doctor-patient conversations, patient surveys or interviews, patient portals, and/or other sources of information. The patient authored text corpus 106 may include conversations between patients and one or more healthcare professionals, interviews of patients, and/or texts that may include relevant information describing opinions, sentiments and points of view related to health topics of patients, and/or other text associated with health-related issues. In some examples, the patient authored text corpus 106 may include text data associated with the entity 110.

The processor 120 may further obtain or receive patient authored health data 107 from the data sources 102, where the patient authored health data 107 may include a plurality of data associated with one or more patients. The data sources 102 that may provide the patient authored health data 107 may include databases storing clinical data and/or health data generated by patients. The patient authored health data 107 may include clinical data such as patient structured data from electronic medical records, electronic health records, or hospital information systems. The patient authored health data 107 may further include patient generated health data such as health related data created, recorded or gathered by or from patients, family members, or other caregivers, to help address health concerns, health history, treatment history, biometric data, symptoms, lifestyle choices, and/or other types of information related to the health of the patients. In some examples, the patient authored health data 107 may include data associated with the entity 110.

In an example, the patient authored text corpus 106 and the patient authored health data 107 may be obtained or received from different sources. In some examples, portions of the patient authored text corpus 106 may not be associated to particular patients. For example, the patient authored text corpus 106 may include text from conversations between doctors and patients, without indicating the identities of the doctors and the patients within the conversations. In some examples, the patient authored health data 107 may include identities of patients and corresponding health data. In some examples, the system 100 may also receive other data such as audio data including audio recordings of doctor-patient conversations, patient surveys or interviews, and/or other sources of information recorded as audio data.

Obtaining or receiving of information pertaining to patients would be performed with proper permissions from respective parties involved, for example, including the patients. For example, prior to retrieving patient authored text corpus 106 and patient authored health data 107, the processor 120 may first send a data retrieval request to one or more data sources 102. Upon receiving approval of the data retrieval request from the data sources 102, where the approval may be issued by the patients who authored the patient authored text corpus 106 and the patient authored health data 107, the processor 120 may begin to retrieve patient authored text corpus 106 and patient authored health data 107 from the data sources 102.

In an example, execution of the phase 126 may include the processor 120 annotating the patient authored text corpus 106 to generate annotated text data 108. The processor 120 may annotate the patient authored text corpus 106 in accordance with the health behavior change model 112 and a communicative taxonomy among taxonomy data 113. In some examples, the processor 120 may pre-process the patient authored text corpus 106 prior to performing the annotating, such that the processor 120 may annotate the pre-processed portions or fragments of the patient authored text corpus 106.

The processor 120 may use the annotated text data 108 as training data to train a stage engagement communicative model (herein "communicative model 131"), where the communicative model 131 may be a model related to a communicative taxonomy of each stage of behavior change of one or more patients. For example, an input to the communicative model 131 may be a discussion between a patient and a healthcare professional concerning treatment or clinical condition, and the discussion may include particular communicative action characteristics such as utterance characteristics from the patient. The communicative model 131 may determine an outcome to classify the behavior of the patient (as positive or negative perception of patient engagement, or particular disease, or health related issues associated with the patient) in the discussion based on the tone, text, communicative actions, and/or other characteristics within the discussion. In an example, the processor 120 may apply machine learning instructions among the engagement instructions 124 to train the communicative model 131 (further described below).

The processor 120 may further define a set of patient profiles 140 based on the communicative model 131, the patient authored text corpus 106, and the patient authored health data 107 (further described below. Each patient profile 140 may include data indicating a personality, preference of learning, preference of communication type, and/or other information and preferences, of a corresponding patient. The processor 120 may use the communicative model 131 and the set of patient profiles 140 to generate the knowledge base 134 of the knowledge based system 130. In some examples, the communicative model 131, the patient profiles 140, and the knowledge base 134 may be continuously updated by the system 100 when the patient authored text corpus 106 and the patient authored health data 107 are updated. In some examples, the knowledge base 134 may be represented as an object model, such as ontology and/or graphs. The knowledge base 134 may represent facts inferred from the patient authored text corpus 106, the patient authored health data 107, and the set of patient profiles 140. In some examples, the knowledge base 134 may indicate facts relating to one or more populations, such as patients from particular groups and/or locations, and may also indicate facts relating to individual patients, such as the entity 110.

The knowledge based system 130 may include the inference engine 132 and the knowledge base 134, wherein the inference engine 132 may be developed by the system 100 (further described below). The knowledge base 134 may be coupled to the inference engine 132, where the inference engine 132 may be a set of inference rules (that may be defined by engagement strategy instructions 124) executable by the processor 120 infer new information from the knowledge base 134. The processor 120 may complete the phase 126 upon the construction of the knowledge based system 130.

In some examples, the phase 128 may be triggered by a receipt of a request 105. Execution of the phase 128 may include the processor 120 determining, or receiving, an engagement degree 160 and an engagement strategy score 170 associated with the entity 110. The engagement degree 160 may indicate a degree, or level, of engagement by the entity 110 in a patient engagement process (e.g., how engaged is the entity 110) In an example, a current engagement stage of the entity 110 relative to the engagement process, along with opinions or perceptions of the entity 110 on health topics or the engagement process, may be used by the processor 120 to determine the engagement degree 160. The engagement strategy score 170 may indicate a score, or effectiveness, of a current strategy being implemented, or planning to be implemented, on the entity 110 to achieve a next engagement stage in the engagement process. The processor 120 may input the patient profile 140, the engagement degree 160, and the engagement score 170, into the knowledge based system 130. The processor 120 may execute the knowledge based system 130, such as by applying the inference rules of the inference engine 132, on the inputted data and using knowledge base 134, to generate the patient engagement communicative strategy 180. The patient engagement communicative strategy 180 may include a set of data indicating, or specifying, one or more of the patient profile 140 of the entity 110, a current engagement stage of the entity 110, a next engagement stage within an engagement process being applied on the entity 110, the engagement degree 160, the engagement score 170, a communication scheme that may include a suggestion of strategies for achieving the next engagement stage, and/or other data that may provide suggestions to improve the patient engagement of the entity 110.

The system 100 may deploy the knowledge based system 130 to an interactive device, such as a computer device implementing a chatbot, in order for the interactive device to receive inquiries on one or more patients (e.g., the request 105) and determine answers (e.g., the patient engagement communicative strategy 180) to the inquiries. The processor 120 may also be configured to render the data among the patient engagement communicative strategy 180 in order to output, on a display, the answers to inquiries received at the interactive system, or output a report including the patient engagement communicative strategy 180, in order for the user 103 to view the patient engagement communicative strategy 180.

In an example, the user 103 may be a health professional who requests to know (e.g., using the request 105) how much the entity 110 is engaged or satisfied with a conduct treatment that was agreed upon by the health professional and the entity 110, and how to improve communication, such as a talking style, to the entity 110 in order to improve or maintain a high patient engagement. The health professional may also request, as part of the request 105, for an evaluation of conversations between the health professional and the entity 110. The system 100 may receive the request 105, and may present to the health professional the profile of the entity 110 (e.g., the patient profile 140) in order for the health professional to understand better the entity 110 and personalize treatment plans of the entity 110. Also, the health professional may know how much the entity 110 is engaged to planned treatments based on the engagement degree 160 determined by the system 100. In additional to the engagement degree 160, the system 100 may present a current engagement stage and a next engagement stage and the engagement score 170 of one or more strategies to proceed to the next engagement stage, where the next engagement stage may be a goal to improve or maintain the patient engagement of the entity 110. The health professional may view the engagement score 170 of the strategies, and may determine which strategy may require improvement. The system 100 may suggest communication schemes that may facilitate improvement of the strategies, such as communicate with the entity 110 using a recommended communication tool, method, tone, and/or other strategies.

In an example, the interaction system implementing the system 100 or the knowledge based system 130 may conduct a teleconsultation with the health professional to provide consultation on strategies to improve the patient engagement of the entity 110.

In an example, the system 100 may provide an analysis on the engagement of a particular population, such as a group of patients. The patient engagement communicative strategy 180 generated by the system 100 may present information and prioritize interventions with the patients among the population according to their engagement degree and score of the engagement strategy. For example, the patient engagement communicative strategy 180 may indicate a need to communicate with patients among the population that has relatively low engagement degrees before communicating with patients among the population that has relatively high engagement degrees. The health professional, based on the patient engagement communicative strategy 180, may determine whether it is preferable to communicate with the patients directly, or with a care team of the patients. The health professional, based on the patient engagement communicative strategy 180, may use a particular style or tool to communicate with the patients among the population based on the communications scheme suggested by the patient engagement communicative strategy 180. For example, the health professional may use the suggestions in the patient engagement communicative strategy 180 to determine an optimal communication style with patients of different populations.

In an example, a healthcare provider may use the engagement degree 160 provided by the patient engagement communicative strategy 180 to classify clients and to promote various facets of healthcare, such as treatment options, prices, resources, and/or other facets. For example, the healthcare provider may use the communication scheme suggested by the patient engagement communicative strategy 180 to promote healthy habits to help patients with particular health problems (e.g., what types of exercise may be appropriate), plan patient-engagement programs to clients, and promote available resources for the patients, and/or other facets of healthcare.

In an example, a chatbot may implement the system 100 to communicate with the entity 110 directly using the communication scheme suggested by the patient engagement communicative strategy 180. For example, the chatbot may be programmed to speak at a recommended volume, tone, voice, speed, and/or other characteristics, that may lead to an improvement of the patient engagement of the entity 110.

Figure 2:
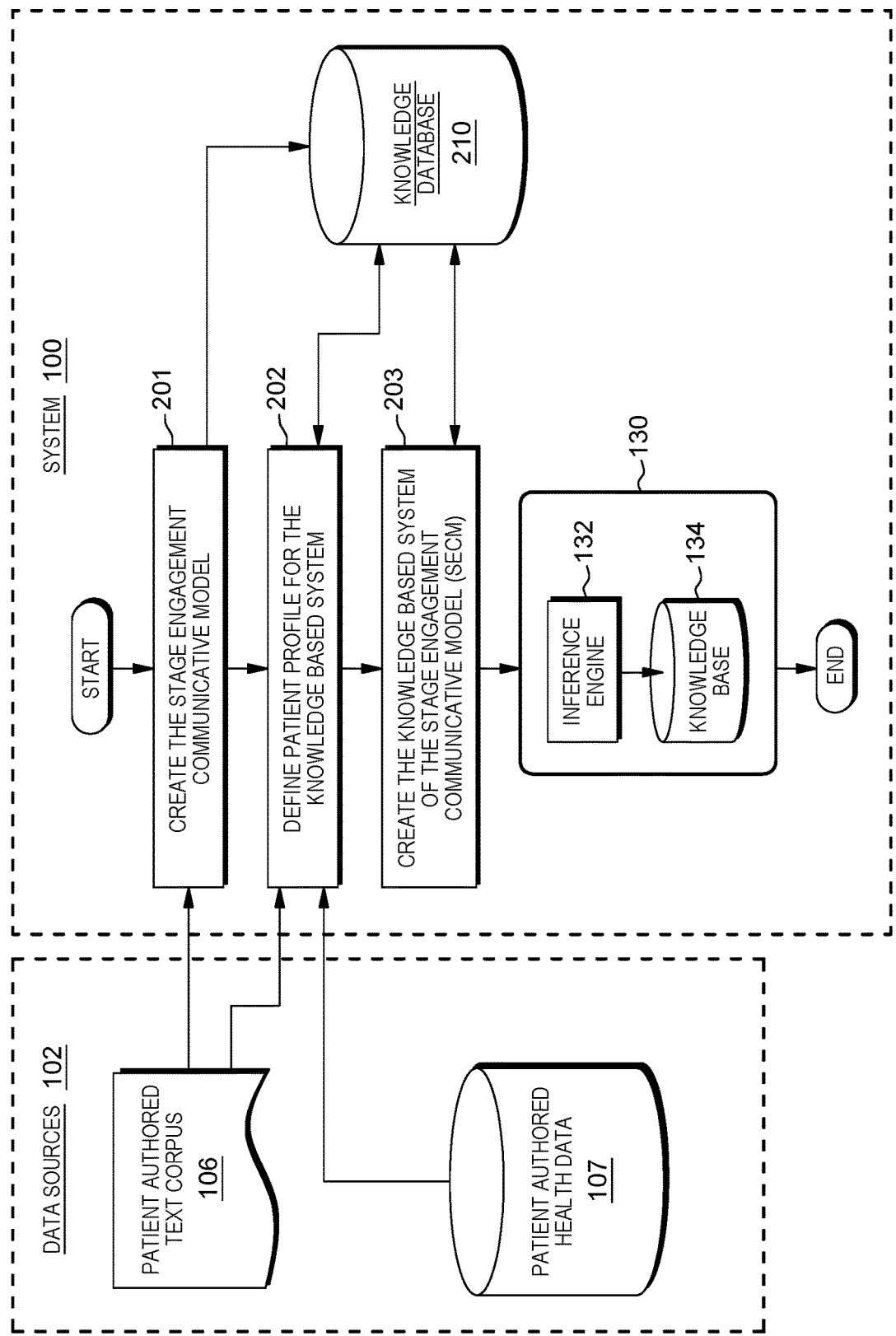
FIG. 2 illustrates an example process of a phase of an implementation of the example system of FIG. 1 in one embodiment.

FIG. 2 illustrates an example process of a phase of an implementation of the example system of FIG. 1, arranged in accordance with at least some embodiments described herein. FIG. 2 may be described below with references to the above descriptions of FIG. 1.

In the example process shown in FIG. 2, the phase 126 of the implementation of the system 100 may start at block 201, where the system 100 may train the communicative model 131. Training of the communicative model 131 may be based on annotated portions of the patient authored text corpus 106 (e.g., annotated text data 108). The patient authored text corpus 106 may include text data retrieved from social media, healthcare social media, doctor-patient conversations, patient surveys or interviews, patient portals, texts that contains relevant information describing patient's opinions, sentiments and points of view related to health topics related with diseases and/or other data sources.

In an example, the system 100 may identify particular pieces of data that may be needed to create the knowledge base 134, and may store the identified data in a knowledge database 210. The system 100 may receive the patient authored text corpus 106 for the first time, the system 100 may annotate the patient authored text corpus 106 according to the health behavior change model 112 in order to generate the annotated text data 108. Examples of the health behavior change model 112 may include transtheoretical model, health belief model, theory of planned behavior, and/or other behavior models. When the system receives the same patient authored text corpus 106 a second time, or at subsequent times, annotation may not be necessary because annotation of the same patient authored text corpus 106 may already be recorded in the knowledge base 134. The processor 120 may store the annotated text data 108 in the knowledge database 210. The knowledge database 210 may be configured to store data that is necessary to create the knowledge base 134. By storing data necessary to create and/or update the knowledge base 134 in the knowledge database 210, the processor 120 may access data from the knowledge database 210 directly to create and/or update the knowledge base 134, and may avoid performing excessive operations to retrieve, process, and annotate, data such as the patient authored text corpus 106 during creation and updates of the knowledge base 134. The processor 120 may execute machine learning algorithms to train the communicative model 131 using the annotated text data 108 stored in the knowledge database 210.

The phase 126 may continue from block 201 to block 202, where the system 100 may define a set of patient profiles 140. The system 100 may define a plurality of patient profiles 140 based on the patient authored text corpus 106 and the patient authored health data 107 retrieved from the data sources 102. The patient authored health data 107 may include clinical data, patient generated health data, and/or other data associated with the health of a patient. The patient authored health data 107 may also include medical record (EMR), electronic health record (EHR), data from hospital information systems (HIS), health-related data created, recorded or gathered by or from patients or family members or other caregivers of the patient, information that may help to address a health concern, health history, treatment history, biometric data, symptoms, and lifestyle choices, and/or other information. In some examples, the patient authored health data 107 may be distinct from data generated in clinical settings, and may be generated through encounters with providers in various ways. For example, a patient may be responsible for capturing or recording particular data associated with his or her own health, or the patient may decide how to share or distribute, or which data to share and distribute, the data generated by the patient to health care providers and others.

In some examples, the system 100 may generate the patient profile 140 based on the annotated text data 108 stored in the knowledge database 210 in addition to using the patient authored health data 107. In some examples, the system 100 may store the patient profile 140 in the knowledge database 210. The plurality of patient profiles 140 generated and stored in the knowledge database 210 may include patient profiles of one or more patients. In some examples, the patient profiles 140 may be indexed based on identifications of each patient in the patient authored health data 107.

The phase 126 may continue from block 202 to block 203, where the system 100 may create, or generate, the knowledge base 134 based on the data stored in the knowledge database 210. The knowledge base 134 may include a set of structured data, where each piece of data may represent an object, and each object may include one or more pointers that point to another object among the knowledge base 134. The objects represented in the knowledge base 134 may include entities (e.g., a doctor, a patient, and/or other types of entity), items (e.g., tools such as medical tools, treatment tools, therapy tools, computing devices, and/or other items), facts (e.g., a preference, an event, and/or other types of facts), and/or other types of objects. By creating the knowledge base 134 to represent the objects, and assigning pointers for the objects to express relationships among the objects, the knowledge base 134 may provide a pool of data representing medical history of patients, preferences of the patients, demographics of patients, and/or other facts of the patients.

The processor 120 may create the knowledge base 134 based on the communicative model 131, such as by populating the knowledge base 134 with outcomes determined by the communicative model 131 and assigning pointers to connect the outcomes to corresponding inputs (e.g., such as the annotated text data 108). Further, the processor 120 may create the knowledge base 134 based on the plurality of patient profiles 140 stored in the knowledge database 210, such as by populating the knowledge base 134 with entities and facts indicated by each of the patient profiles 140. By creating the knowledge base 134 based on both the communicative model 131 and the patient profiles 140, the knowledge base 134 may map portions of the patient profiles 140 to inputs and outputs of the communicative model 131, such that the connections may indicate how a patient may behave in particular situations. The processor 120 may continuously retrain the communicative model 131 based on new data being received, from the data sources 102, at the system 100, and may update the knowledge base 134 based on the retrained communicative model.

The processor 120 may also develop the inference engine 132 (further described below). The inference engine 132 may include inference rules, or logic, that may be defined by the engagement instructions 124, and may be executable by the processor 120 to infer new data from the knowledge base 134. For example, an input to the knowledge based system 130 may be an inquiry on a communication preference of the entity 110, and the processor 120 may apply the inference rules in the inference engine on the knowledge base 134 to identify data representing the entity 110 and preferred communication method of the entity 110. In some examples, the processor 120 may create or update the inference engine 132 based on changes to the communicative model 131, patient profile 140, and the engagement degree 160 (described below) and the engagement strategy score 170 (described below).

Figure 3:
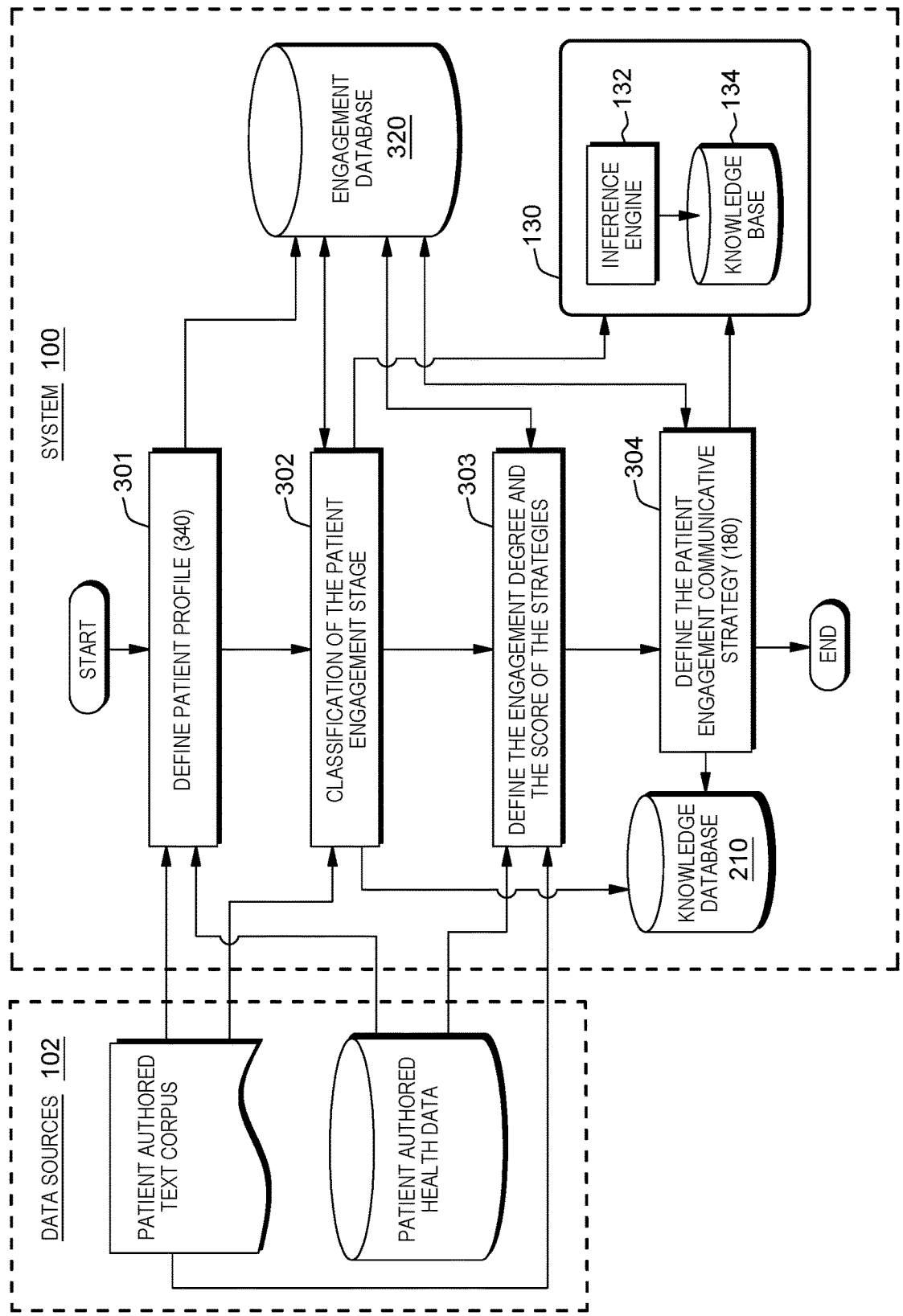
FIG. 3 illustrates an example process of a phase of an implementation of the example system of FIG. 1 in one embodiment.

FIG. 3 illustrates an example process of a phase of an implementation of the example system of FIG. 1, arranged in accordance with at least some embodiments described herein. FIG. 3 may be described below with references to the above descriptions of FIGS. 1-2.

In the example process shown in FIG. 3, the phase 128 of the implementation of the system 100 may start at block 301. In some examples, the block 301 may be triggered by the receipt of the request 105 at the system 100. At block 301, the processor 120 may define the patient profile 140 of the entity 110 based on the patient authored text corpus 106 and the patient authored health data 107. The processor 120 may store the patient profile 140 of the entity 110 in an engagement database 320, where the engagement database 320 may be configured to store data that may be necessary to generate the patient engagement communicative strategy 180 to fulfill request 105. In some example, the patient profile 140 of the entity 110 may already be stored in the engagement database 320 prior to the start of block 301, such that at block 301, the processor 120 may identify and retrieve the patient profile 140 of the entity 110 from the engagement database 320.

The phase 128 may continue from block 301 to block 302, where the system 100 may classify a patient engagement stage, such as defining a current patient engagement stage of the entity 110, based on the patient authored text corpus 106 and the data stored in the engagement database 320. In some examples, a patient engagement process may include a plurality of stages. In an example, stages among a first patient engagement process may include inform, involve, and collaborate. In another example, stages among a second patient engagement process may include inform, engage, empower, collaborate, and support. The stages of the patient engagement process being used to implement the system 100 may be based on a desired implementation of the system 100. In some examples, the engagement stages may be classified according to previously chosen model of behavior change. For example, a Transtheoretical Model of Behavior Change (TTM) may include five engagement stages: pre-contemplation, contemplation, preparation, action and maintenance. The classification of the patient engagement stage will be described in more detail below.

The phase 128 may continue from block 302 to block 303, where the system 100 may determine the engagement degree 160 and the score of the strategies (engagement strategy score 170). In an example, portions of the patient authored text corpus 106 may be annotated by the processor 120 to generate the annotated text data 108, where the annotated text data 108 may be classified based on perceptions and polarity, such as positive and negative perceptions, views, opinions, of health-related issues. The processor 120 may classify the annotated text data into one or more of the perceptions of the health behavior change model 112. For example, a piece of annotated text data 108 may indicate a negative perception of a particular disease from the entity 110, such that the processor 120 may classify the piece of annotated text data 108 into a negative perception category. The processor 120 may determine the engagement degree 160 based on the classification of the annotated text data 108 into the health behavior change model 112, and based on the data stored in the engagement database 320. The engagement degree 160 may be reflective of how engaged is the entity 110 in an engagement process being implemented for the entity 110. For example, results of the classification of the annotated text data 108 may include perceptions classified as positive or negative to a patient engagement contribution, such as a positive perception indicates an increase in patient engagement and a negative perception indicates a decrease in patient engagement. Thus, a patient with a significant amount of negative perceptions may result in a low engagement degree, which may be reflective of low patient engagement, or reflective of possible unwillingness from the patient to engage or continue to engage in his or her own health treatments.

In an example, the engagement strategy score 170 may be scores assigned to the entity 110 based on a set of World Health Organization (WHO) rules. The system 100 may store the engagement degree 160 and the engagement strategy score 170 in the engagement database 320. In some examples, information among the patient authored health data 107, such as diagnosis, current health state, and/or other information, may be used by the processor 120 to determine the engagement score 170 of each intervention strategy applicable to the patient (further described below).

The phase 128 may continue from block 303 to block 304, where the system 100 may define the patient engagement communicative strategy 180 using the knowledge base 134, the patient profile 140, the engagement degree 160, and/or the engagement strategy score 170. The patient engagement communicative strategy 180 may provide the user 103 recommendations and strategies to communicate with the entity 110.

Figure 4:
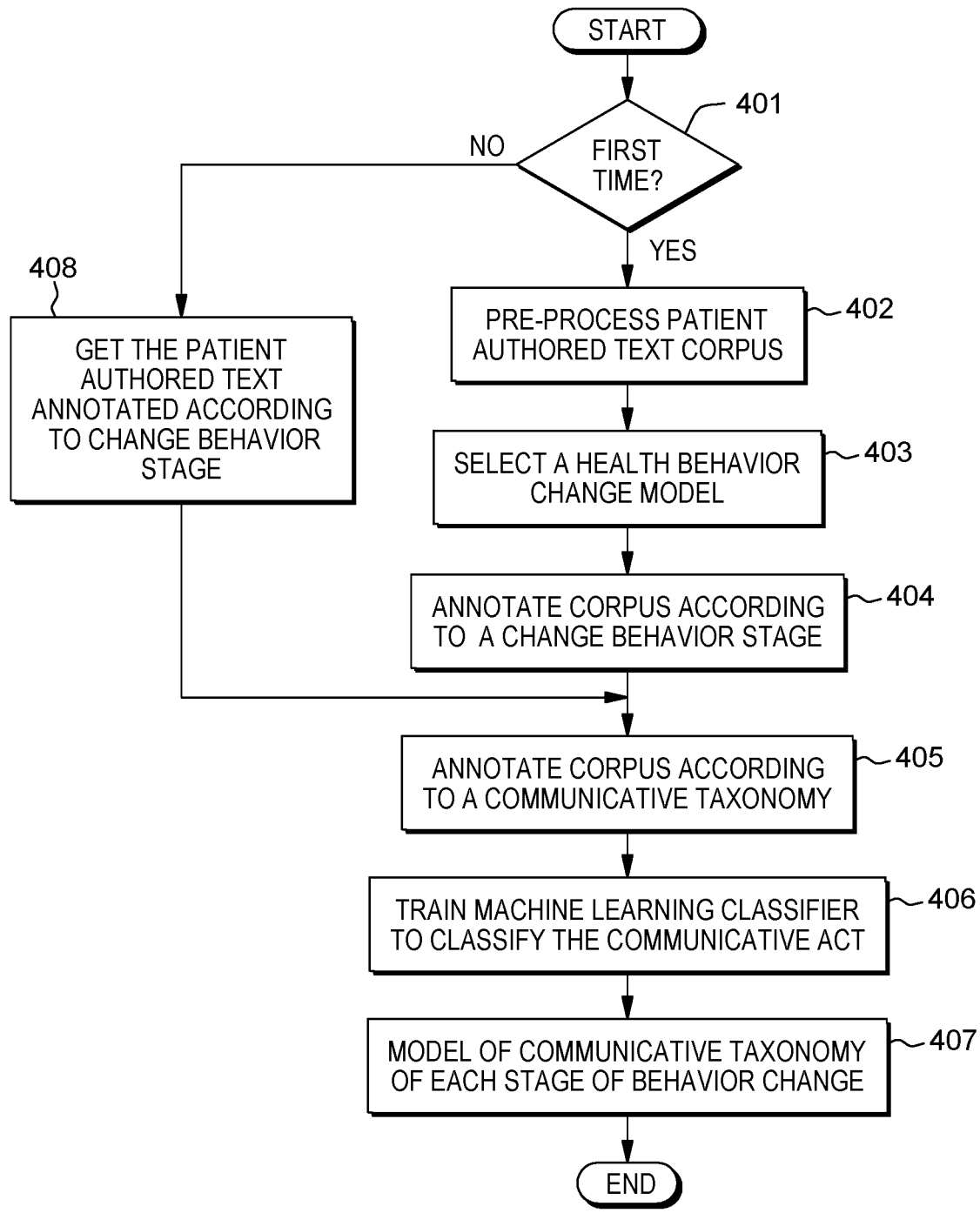
FIG. 4 illustrates an example process of implementing the example system of FIG. 1 to train a stage engagement communicative model in one embodiment.

FIG. 4 illustrates an example process of implementing the example system of FIG. 1 to train a stage engagement communicative model, arranged in accordance with at least some embodiments described herein. FIG. 4 may be described below with references to the above descriptions of FIGS. 1-3.

The processor 120 of the system 100 may train the stage engagement communicative model (communicative model 131) by implementing an example process shown in FIG. 4, which includes blocks 401, 402, 403, 404, 405, 406, 407, and 408. In an example, the blocks 401, 402, 403, 404, 405, 406, 407, and 408 may be components of the block 201 shown in FIG. 2 corresponding to training the model 131 in the phase 126.

At block 401, the processor 120 may receive the patient authored text corpus 106. The processor 120 may determine whether the patient authored text corpus 106 is received at system 100 for the first time. For example, the processor 120 may compare one or more portions of the received patient authored text corpus 106 with data stored in the knowledge database 210 to determine whether the one or portions are already stored in the database 210. If the processor 120 determines that it is the first time the system 100 receives the patient authored text corpus 106, the processor 120 may proceed to block 402.

At block 402, the processor 120 may pre-process the received patient authored text corpus in order to prepare the patient authored text corpus 106 for training the communicative model 131. Various text pre-processing techniques may be applied by the processor 120 to clean and prepare the patient authored text corpus 106 for later classification. Some examples of pre-processing the patient authored text corpus 106 may include sentence split, parsing sentences, stemming, and/or other text processing techniques.

At block 403, the processor 120 may select a health behavior change model 112 from a plurality of models that may include transtheoretical model, health belief model, theory of planned behavior, and/or other health-related behavior models. The plurality of models may be stored in the memory 122, and selection criteria that may be used by the processor 120 may be part of the engagement instructions 124. In some examples, blocks 402, 403 may be performed by the processor 120 in an arbitrary order or simultaneously. The selection of the health behavior change model may provide a foundation for patient adherence assessment as the plurality of health behavior change models include indications of the perceptions, or points of view, of the patients regarding medical infrastructure, disease, treatment and the patients themselves.

Upon completion of blocks 402 and 403, the process to train the communicative model 131 may proceed to block 404. At block 404, the processor 120 may annotate the patient authored text corpus 106 pre-processed at block 402 according to the health behavior change model 112 chosen at block 403. The processor 120 may annotate the pre-processed patient authored text corpus 106 to generate the annotated text data 108. The processor 120 may annotate the patient authored text corpus 106 according to perceptions (e.g., by severity, vulnerability, benefits, etc.) of the selected health behavior change model 112. For example, if a fragment of the patient authored text corpus 106 indicates that the entity 110 has doubts on a treatment plan, according to the health behavior change model 112, the processor 120 may annotate the fragment by annotating the treatment plan with a negative interpretation. The processor 120 may store the annotated text data 108 in the database 210. In some examples, the processor 120 may be configured to annotate fragments of the patient authored text corpus 106 by adding or attaching metadata to the fragments, where the metadata may indicate an interpretation of the annotated fragment. The combination of the metadata and the annotated fragment may be parts of the annotated text data 108.

Returning to block 401, if the processor 120 determines that it is not the first time the system 100 receives the patient authored text corpus 106, the process to train the communicative model 131 may proceed to block 408. In some examples, the system 100 may perform an update to the knowledge base 134 in response to the determination that it is not the first time the system 100 receives the patient authored text corpus. At block 408, the processor 120 may retrieve the patient authored text corpus 106 that may already be annotated and stored in the knowledge database 210. The process to train the model 131 may proceed to block 405 from block 408.

At block 405, the processor 120 may further annotate the patient authored text corpus 106 annotated in block 404 to generate the annotated text data 108. The processor 120 may further annotate the patient authored text corpus 106 annotated in block 404 according to a communicative taxonomy, such as speech act, rhetoric approaches, ISO standards such as ISO 24617, primitives such as dialog act markup in several layers (DAMSL, SWBD-DAMSL), and/or other communicative or linguistic taxonomy. For example, a fragment among the patient authored text corpus 106 that includes words or expressions of uncertainty may be annotated as a negative perception. In some examples, the processor 120 may execute the blocks 404 and 405 in an arbitrary order or simultaneously. The engagement instructions 124 may include instructions for the processor 120 to determine which communication taxonomy may be used to annotate the patient authored text corpus. In some examples, speech acts or dialog acts may be characterizations of actions performed by a speaker during a conversation or a dialog. The characterizations provide representations of conversational function and may be analyzed by computer systems, such as the system 100, in order to develop models (e.g., the communicative model 131) that may be executed to automatically interpret various communicative acts and to determine meaningful responses or reactions.

At block 406, the processor 120 may apply machine learning algorithms, using the annotated text data 108 as inputs to the machine learning algorithms, to train the communicative model 131. For example, the annotated text data 108 may include fragments of the patient authored text corpus 106 and corresponding annotations indicating an interpretation of the fragments (e.g., interpretation such as positive or negative opinion towards a health topic being discussed in the fragments). The fragments among the annotated text data 108 and corresponding interpretations may be used as training set that may be inputted into a machine learning algorithm to train the communicative model 131. As such, the communicative model 131 may be a classifier to classify communicative acts, such as fragments of conversations included in the patient authored text corpus 106, into categories such as positive or negative perceptions. Machine learning algorithms that may be applied by the processor 120 to train the communicative model 131 may include naïve Bayes algorithm, support vector machines (SVM), multilayer perceptron (MLP) and/or other machine learning algorithms.

At block 407, a completion of the training of the communicative model 131 may provide a model of communicative taxonomy for each stage of behavior change corresponding to the one or more patients. In some examples, the communicative model 131 may be an automatic text classifier that can be executed, such as by the processor 120, to classify perceptions indicated by the selected health behavior change model 112 into categories of communicative acts.

Figure 5:
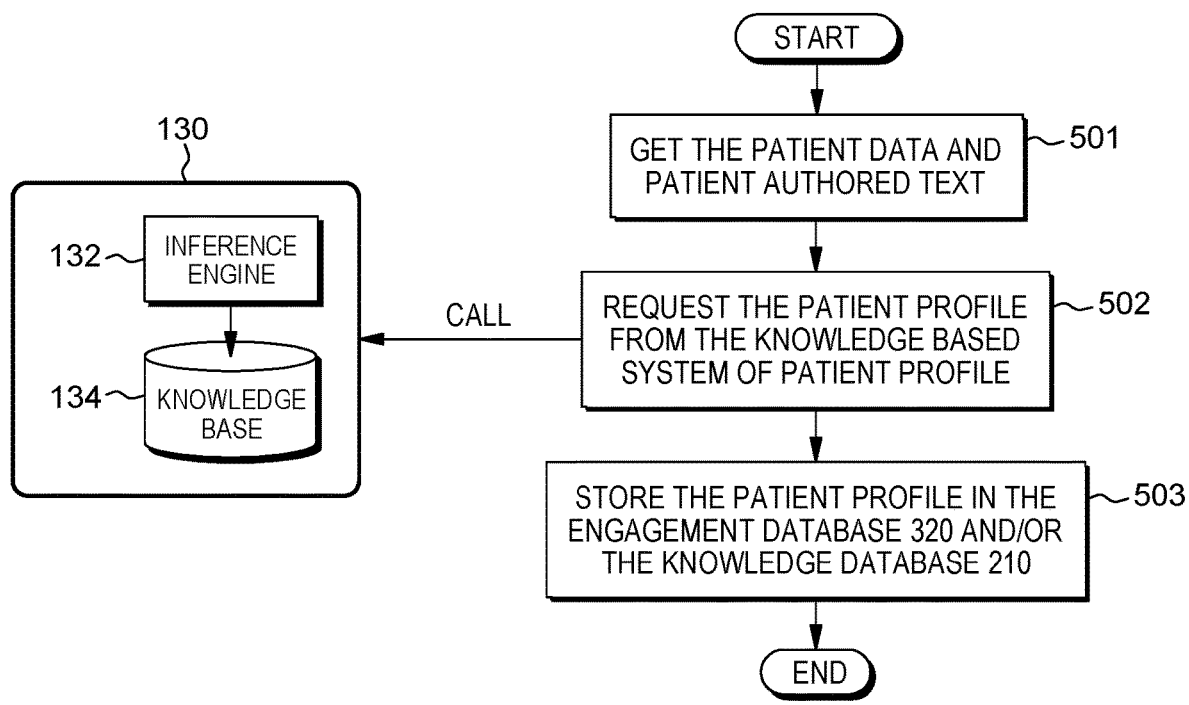
FIG. 5 illustrates an example process of implementing the example system of FIG. 1 to define a patient profile in one embodiment.

FIG. 5 illustrates an example process of implementing the example system of FIG. 1 to define a patient profile, arranged in accordance with at least some embodiments described herein. FIG. 5 may be described below with references to the above descriptions of FIGS. 1-4.

The processor 120 of the system 100 may define the patient profile 140 by implementing an example process shown in FIG. 5, which includes blocks 501, 502, and 503.

In some examples, the patient profile 140 may include information of a plurality of attributes of one or more patients, such as facts or demographics of the entity 110.

At block 501, the processor 120 may obtain text data authored by the entity 110, which may be among the patient authored text corpus 106, and the patient authored health data 107 associated with the entity 110. Also at block 501, the processor 120 may obtain the annotated text data 108, such as by annotating the patient authored text corpus 106 and/or retrieving annotated text data 108 corresponding to the entity 110 that are stored in the knowledge database 210 and/or the engagement database 320.

At block 502, the processor 120 may input the data obtained from block 501 into the knowledge based system 130 to infer information about the patients, where the inferred information may be used by the processor 120 to generate one or more patient profiles 140. The processor 120 may apply inference rules in the inference engine 132 on the data received from block 501, and on the knowledge base 134, to infer or generate the patient profiles 140. For example, an input to the knowledge based system 130 may be a conversation between a healthcare professional and a patient suffering from a particular illness. The processor 120 may execute the inference engine 132 to analyze data and outputs from the conversation in order to infer that the patient learns best by examples and likes a clear and precise style of communication. As such, based on the patient authored text corpus 106 and the knowledge base 134, the inference engine 132 may infer the information to generate patient profiles 140. The knowledge based system 130 may send the inferred information to the processor 120. The processor 120 may continue to execute the knowledge based system 130 to infer information of one or more patients to generate the patient profiles 140, such as calling for the knowledge based system 130 to infer information relating to personality, preference of learning, and/or other information related to the patient. In an example, the processor 120 may call the knowledge based system 130 by executing the inference rules defined by the inference engine 132 of the knowledge based system 130.

At block 503, upon a completion of creating the patient profile 140, the processor 120 may store the patient profile 140 in the database 210 and/or the as part of the engagement date 320. The patient profile 140 may be updated by the processor as new information relating to patients are received at system 100. The processor 120 may update the patient profile 140 stored in the database 210 and/or the engagement data 320 as well. By storing updated patient profile 140 in the database 210 and/or the engagement data 320, the processor 120 may continuously update the knowledge base 134 using the most up to date version of the patient profile 140.

Figure 6:
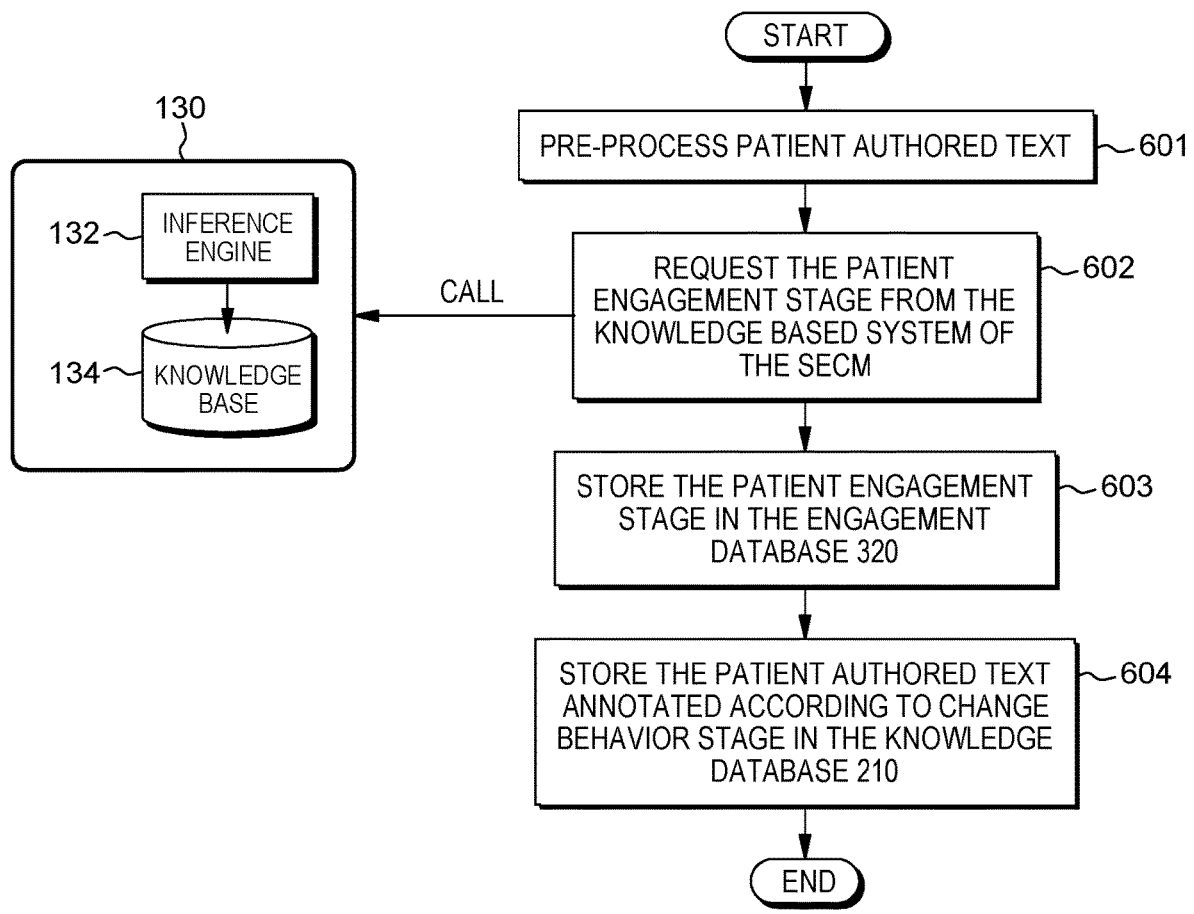
FIG. 6 illustrates an example process of implementing the example system of FIG. 1 to classify a patient engagement stage in one embodiment.

FIG. 6 illustrates an example process of implementing the example system of FIG. 1 to classify a patient engagement stage, arranged in accordance with at least some embodiments described herein. FIG. 6 may be described below with references to the above descriptions of FIGS. 1-5.

The processor 120 of the system 100 may classify an engagement stage of the entity 110, such as determining a current engagement stage of the entity 110 within a patient engagement process, by implementing an example process shown in FIG. 6, which includes blocks 601, 602, 603, and 604.

Block 601 may be similar to block 402 shown in FIG. 4, where the processor 120 may pre-process fragments of the patient authored text corpus 106 associated with the entity 110.

The process to classify a current engagement stage may proceed from block 601 to block 602. At block 602, the processor 120 may call the knowledge based system 130 to inquire the current patient engagement stage of the entity 110. In some examples, when the current engagement stage of the entity 110 is not stored in the engagement database 320, the processor 120 may send the pre-processed data from the block 601 to the knowledge based system 130. The processor 120 may analyze the pre-processed data received at the knowledge based system 130 to determine the current engagement stage of the entity 110. The processor 120 may classify the received engagement stage within an engagement process. For example, the processor 120 may classify the received engagement stage into one of the stages among an engagement process including the stages inform, engage, empower, collaborate, and support.

The process to classify a current engagement stage may proceed from block 602 to block 603. At block 603, the processor 120 may stored the current engagement stage determined by the knowledge based system 130 in the engagement database 320.

In some examples, prior to block 602, the current engagement stage of the entity 110 may be stored in the engagement database 320, such that the processor 120 may identify the current engagement stage from the engagement database 320.

The process to classify a current engagement stage may proceed from block 603 to block 604. At block 604, the processor 120 may stored the annotated text data 108 in accordance with the current engagement stage in the knowledge database 210. For example, particular portions of the annotated text data 108 may be associated with the determined current engagement stage. The processor 120 may store the portions of the annotated text data 108 in the knowledge database 210 for use at a later time, such as retrieving the stored portions of the annotated text data 108 from the knowledge database 210 during a future update of the knowledge based system 130. By updating the knowledge based system 130 using stored annotated text data 108 associated with various engagement stages, the knowledge base 134 may be updated to include data verifying mappings between particular behaviors of the patients with particular engagement stages.

Figure 7:
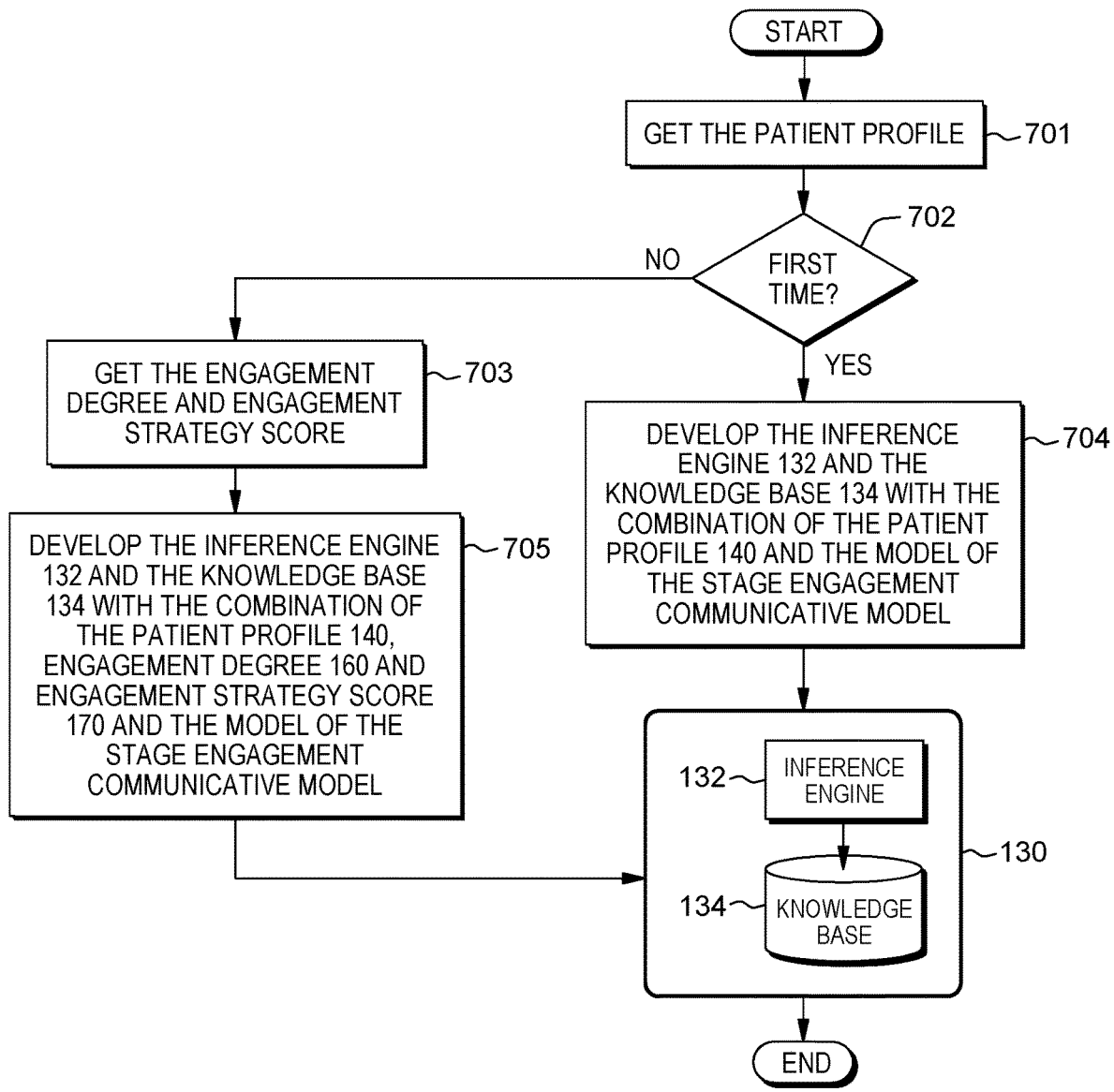
FIG. 7 illustrates an example process of implementing the example system of FIG. 1 to create a knowledge base in one embodiment.

FIG. 7 illustrates an example process of implementing the example system of FIG. 1 to create a knowledge base, arranged in accordance with at least some embodiments described herein. FIG. 7 may be described below with references to the above descriptions of FIGS. 1-6.

The processor 120 of the system 100 may create the knowledge base 134 by implementing an example process shown in FIG. 7, which includes blocks 701, 702, 703, 704, and 705. The process shown in FIG. 7 may be a process to create a knowledge base associated with a particular patient, such as the entity 110.

At block 701, the processor 120 may obtain the patient profile 140 of the entity 110. If the patient profile 140 is stored in the knowledge database 210, the processor 120 may retrieve the patient profile 140 from the knowledge database 210. If the patient profile 140 is not stored in the knowledge database 210, the processor 120 may determine the patient profile 140 as described above.

At block 702, the processor 120 may determine if the patient profile 140 obtained from block 701 is received for a first time. For example, the processor 120 may determine if the patient profile 140 is stored in the knowledge database 210. If the patient profile 140 is received for the first time, the creation of the knowledge base 134 may proceed to block 704. If the patient profile 140 is received for the second or subsequent time, the creation of the knowledge base 134 may proceed to block 703.

At block 704, when the patient profile 140 is received for the first time, the processor 120 may develop the inference engine 132 and create a new knowledge base for the entity 110. For example, the processor 120 may populate the new knowledge base with data from the newly obtained patient profile. The processor 120 may further develop the inference engine 132, such as by defining specific inference rules that may be indicated in the newly obtained patient profile. In some examples, the processor 120 may update the knowledge base 134 based on the newly obtained patient profile.

At block 703, when the patient profile 140 is received for the second or subsequent times, the processor 120 may obtain the engagement degree 160 and the engagement score 170 of the entity 110, which may be stored in the engagement database 320. In some examples, the processor 120 may determine an updated engagement degree 160 and an updated engagement score 170.

Subsequent to block 703, at block 705, the processor 120 may update the inference engine 132 and the knowledge base 134 based on the patient profile 140 obtained from block 701, and based on the engagement degree 160 and the engagement score 170 obtained from block 703. For example, if the entity 110 has a low engagement degree, the processor 120 may populate the knowledge base 134 with facts indicating that the entity 110 may be unwilling to engage in treatments under particular situations.

Figure 8:
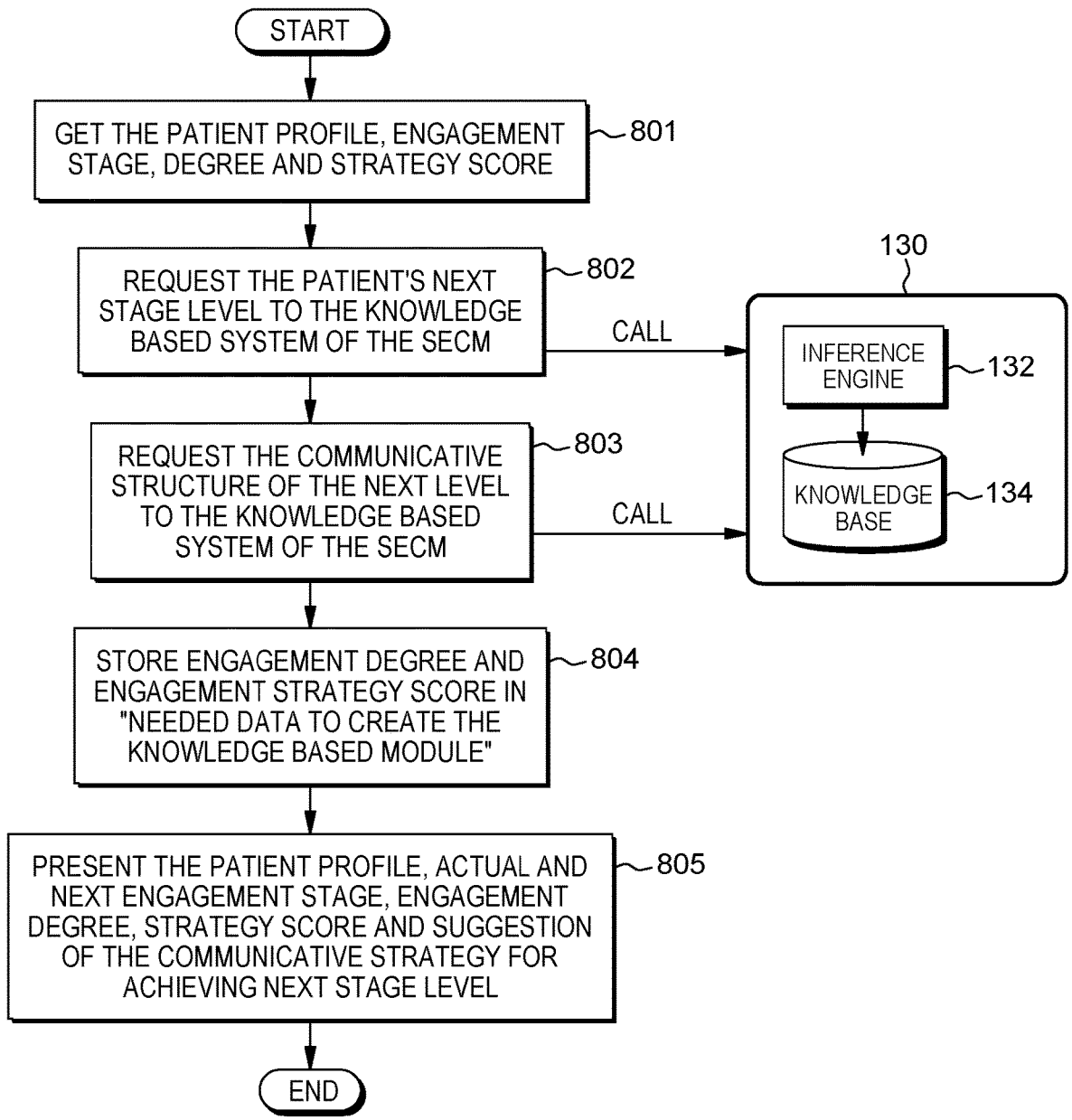
FIG. 8 illustrates an example process of implementing the example system of FIG. 1 to generate a patient engagement communicative strategy in one embodiment.

FIG. 8 illustrates an example process of implementing the example system of FIG. 1 to generate a patient engagement communicative strategy, arranged in accordance with at least some embodiments described herein. FIG. 8 may be described below with references to the above descriptions of FIGS. 1-7.

The processor 120 of the system 100 may generate the patient engagement communicative strategy 180 by implementing an example process shown in FIG. 8, which includes blocks 801, 802, 803, 804, and 805. The example process shown in FIG. 8 may be triggered by the receipt of the request 105 at the system 100.

At block 801, the processor 120 may obtain the patient profile 140, a current engagement stage of the entity 110, the engagement degree 160, and the engagement score 170, from the engagement database 320.

At block 802, the processor 120 may call the knowledge based system 130 to request a next engagement stage of the entity 110. For example, if the engagement process being implemented on the entity 110 includes the stages inform, engage, empower, collaborate, and support, a current engagement stage may be "inform" and a next engagement stage may be "engage". The knowledge base 134 may include data representing the engagement process being implemented on the entity 110, and may include data representing the engagement stages among the engagement process. The inference engine 132 may be include inference rules to detect a sequence of the engagement stages. As such, the processor 120 may send the current engagement stage to the knowledge based system 130, and the inference engine 132 may include inference rules for processor 120 to identify a next engagement stage from the knowledge base 134.

At block 803, the processor 120 may request the knowledge based system 130 to determine a communicative structure for the next engagement stage identified from block 802. For example, if the next engagement stage is "engage", the processor 120 may infer at least a communication tool, a communication style, and/or other communication characteristics, preferred by the entity 110 during the engagement stage of "engage". The processor 120 may store the inferred communication structure in the engagement database 320. In some examples, the inferred communication structure may be reflective of a strategy to proceed to the patient engagement of the entity 110 from the current engagement stage to the next engagement stage.

In some examples, the processor 120 may update the engagement score 170 in order for the engagement score 170 to reflect a predicted effectiveness of the strategy to proceed from the current engagement stage to the next engagement stage. For example, if the entity 110 is not fluent in a first language but is fluent is a second language, a first score of a first strategy to use the first language to communicate with the entity 110 may be lower than a second score of a second strategy to use the second language to communicate with the entity 110.

At block 804, the processor 120 may store the engagement degree 160 and the engagement score 170 in the engagement database 320.

At block 805, the processor may generate the patient engagement communicative strategy 180 by aggregating one or more of the patient profile, the engagement degree 160, the engagement score 170, and the communication structure stored in the engagement database 320. The patient engagement communicative strategy 180 may specify one or more of the patient profile 140, the current engagement stage 160, the current engagement stage, the next engagement stage, the engagement degree 170, and a communication scheme to communicate with the entity 110, where the communication scheme includes a suggestion of strategies for achieving the next engagement stage.

Figure 9:
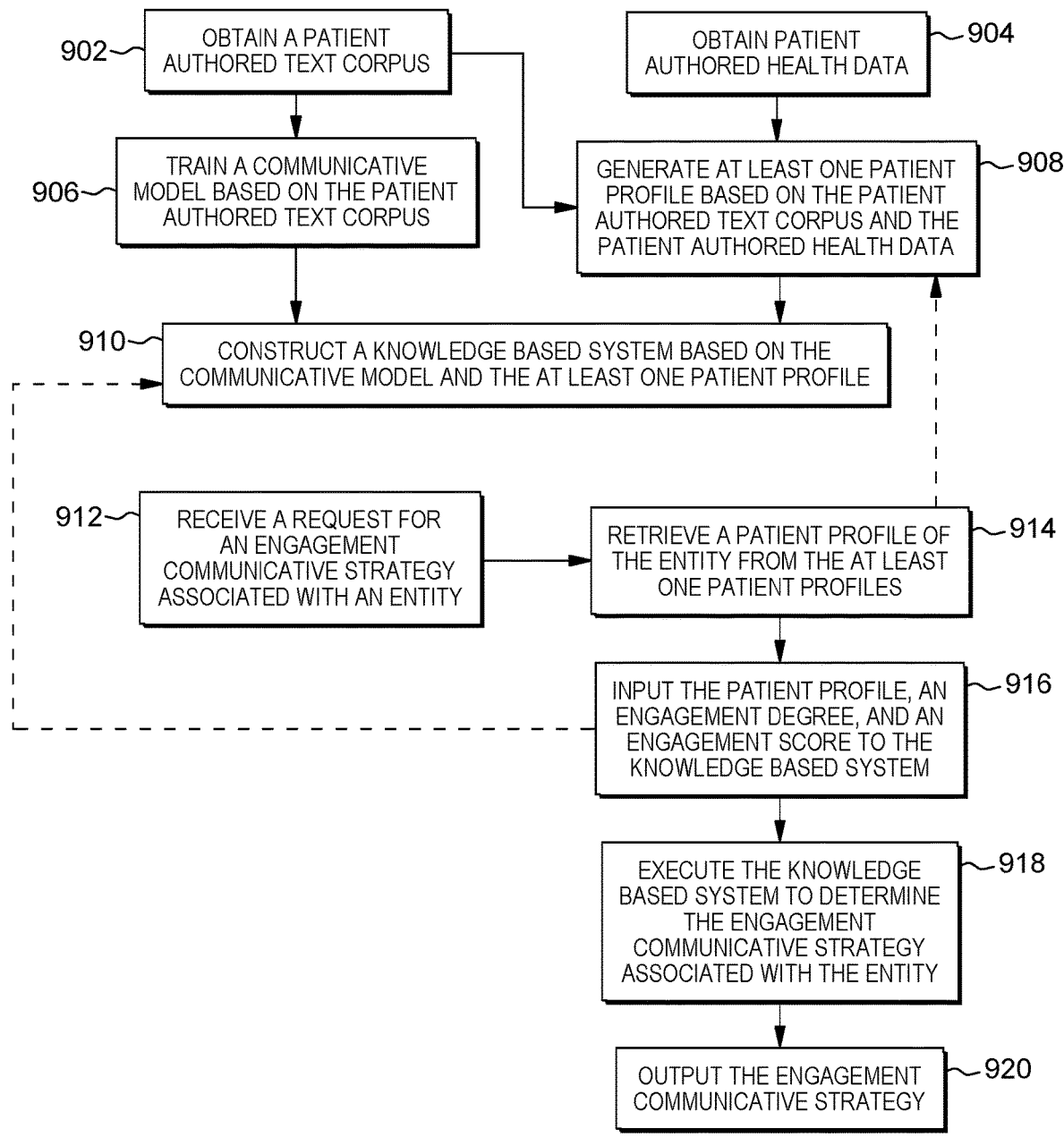
FIG. 9 illustrates a flow diagram relating to patient engagement communicative strategy recommendation in one embodiment.

FIG. 9 illustrates a flow diagram relating to patient engagement communicative strategy recommendation, arranged in accordance with at least some embodiments presented herein. The process in FIG. 9 may be implemented using, for example, computer system 100 discussed above. An example process may include one or more operations, actions, or functions as illustrated by one or more of blocks 902, 904, 906, 908, 910, 912, 914, 916, 918, and/or 920. Although illustrated as discrete blocks, various blocks may be divided into additional blocks, combined into fewer blocks, eliminated, or performed in parallel, depending on the desired implementation.

Processing may begin at block 902, where a processor may obtain a patient authored text corpus from a plurality of data sources.

Processing may continue from block 902 to block 904. At block 904, the processor may obtain patient authored health data from the plurality of data sources.

Processing may continue from blocks 904 to block 906. At block 906, the processor may train a communicative model based on the patient authored text corpus. In some examples, the processor may annotate the patient authored text corpus based on a health behavior model and a communicative taxonomy to generate annotated text data, and may train the communicative model using the annotated text data.

Processing may continue from blocks 906 to block 908. At block 908, the processor may generate at least one patient profile based on the patient authored text corpus and the patient authored health data.

Processing may continue from blocks 908 to block 910. At block 910, the processor may construct a knowledge based system based on the communicative model and the at least one patient profile. The knowledge based system may include an inference engine and a knowledge base.

Processing may continue from blocks 910 to block 912. At block 912, the processor may receive a request for an engagement communicative strategy associated with an entity.

Processing may continue from blocks 912 to block 914. At block 914, the processor may retrieve a patient profile of the entity from the at least one patient profile.

Processing may continue from blocks 914 to block 916. At block 916, the processor may input the patient profile, an engagement degree, and an engagement score to the knowledge based system. The engagement degree may be representative of a level of engagement of the entity in a patient engagement process, and the engagement score may be representative of an effectiveness of a strategy to improve the level of engagement of the entity in the patient engagement process Processing may continue from blocks 916 to block 918. At block 918, the processor may execute the knowledge based system to determine the engagement communicative strategy associated with the entity based on the patient profile, the engagement degree, and the engagement score.

Processing may continue from blocks 918 to block 920. At block 920, the processor may output the engagement communicative strategy. The engagement communicative strategy specify one or more of a communication scheme to communicate with the entity, the patient profile, the current engagement stage, a next engagement stage, the engagement degree, and the engagement score. The communication scheme may include a suggestion of strategies for achieving the next engagement stage.

In some examples, the processor may perform the blocks 902, 904, 906, 908, and 910 continuously in order to retrain the communicative model, and to update the knowledge base of the knowledge based system when new data is received at blocks 902 and 904. The processor may perform the blocks 902, 904, 906, 908, and 910 continuously, regardless of the operation status of blocks 912, 914, 916, 918, and 920. For example, operations of the blocks 912, 914, 916, 918, and 920 may continue even if the processor is retraining the communicative model, and receipt of the request at block 912 may not stop the retraining process.

Figure 10:
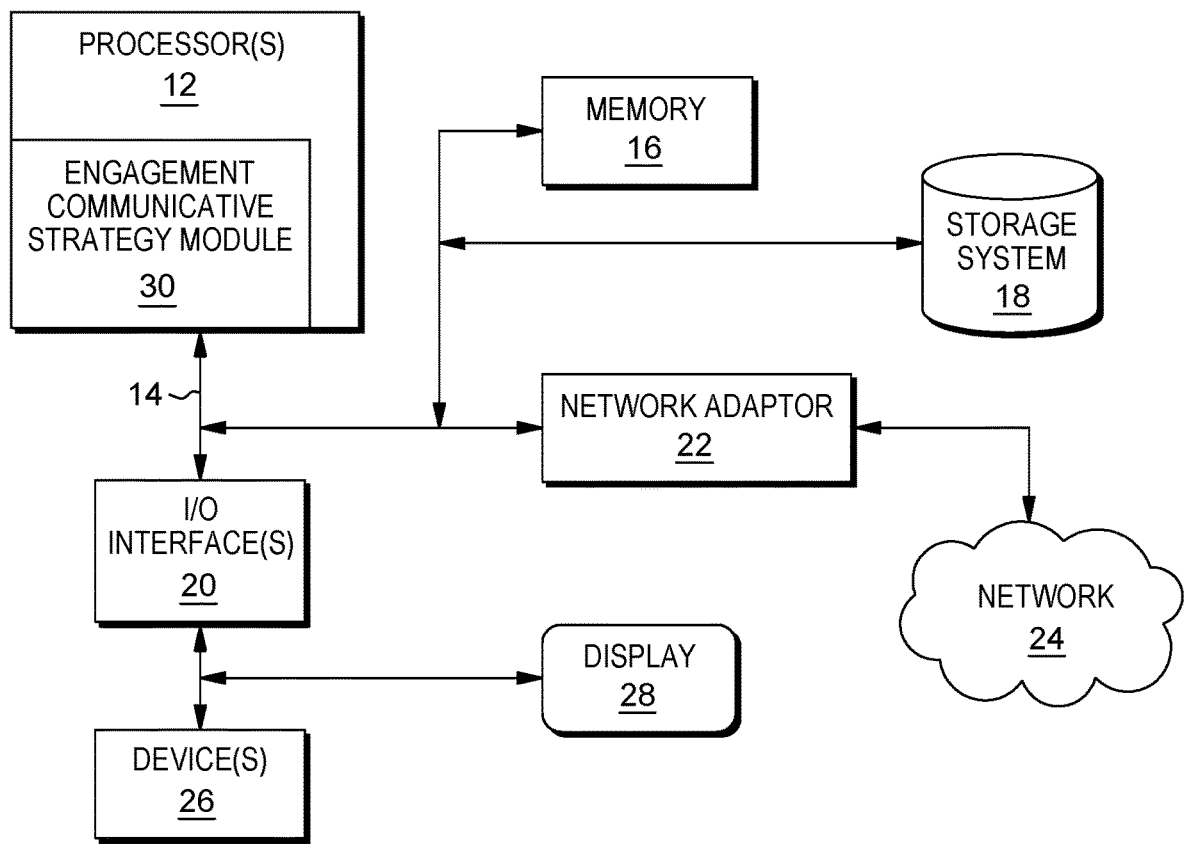
FIG. 10 illustrates a schematic of an example computer or processing system that may implement patient engagement communicative strategy recommendation in one embodiment.

FIG. 10 illustrates a schematic of an example computer or processing system that may implement patient engagement communicative strategy recommendation in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 6 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, supercomputers, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 (e.g., engagement communicative strategy module 30) that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 11:
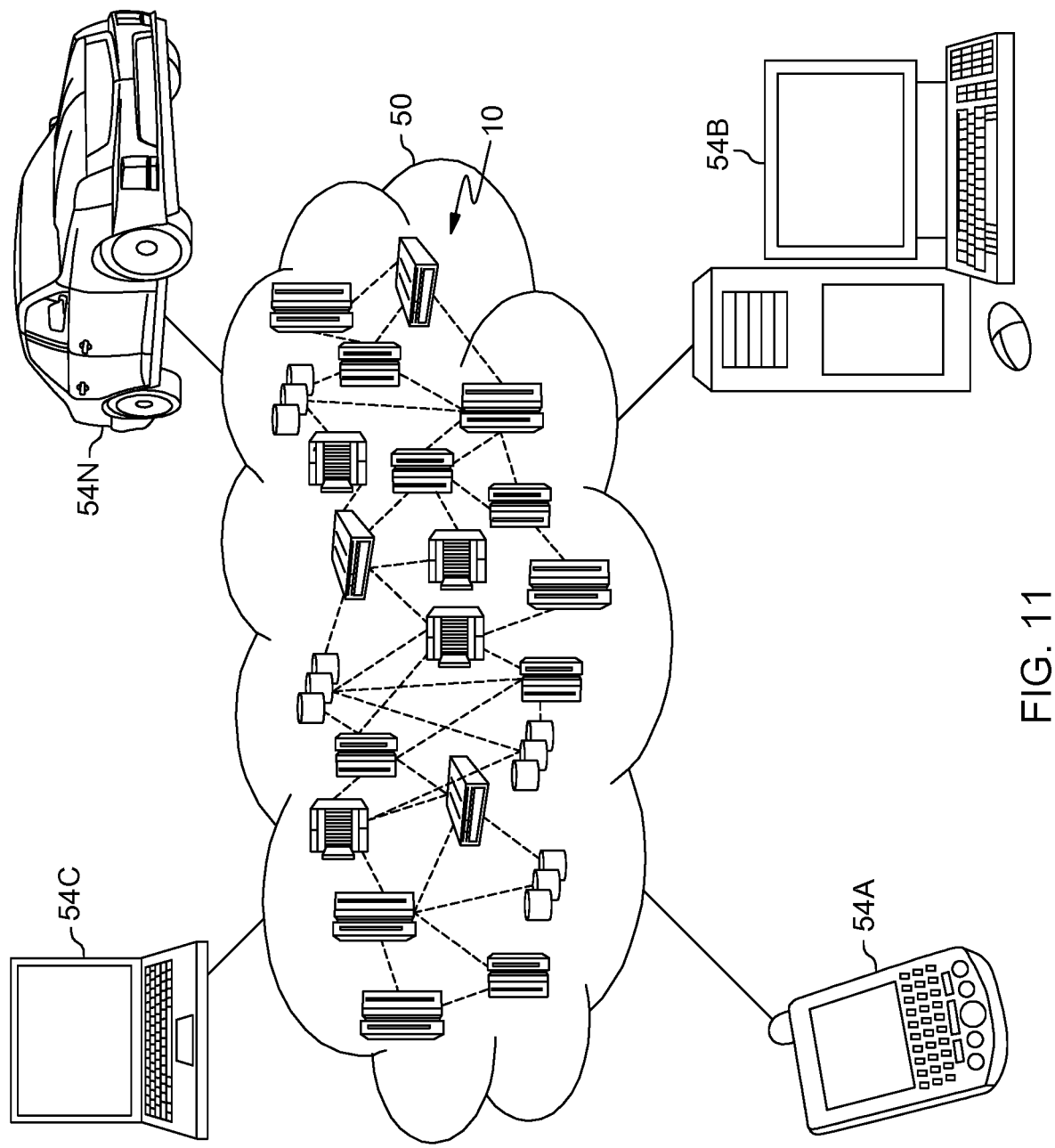
FIG. 11 depicts a cloud computing environment according to an embodiment of the present invention.

FIG. 11 depicts a cloud computing environment according to an embodiment of the present invention. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 11, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 11 are intended to be illustrative only and that computing nodes 10 and cloud computing environment 50 can communicate with any type of computerized device over any type of network and/or network addressable connection (e.g., using a web browser).

Figure 12:
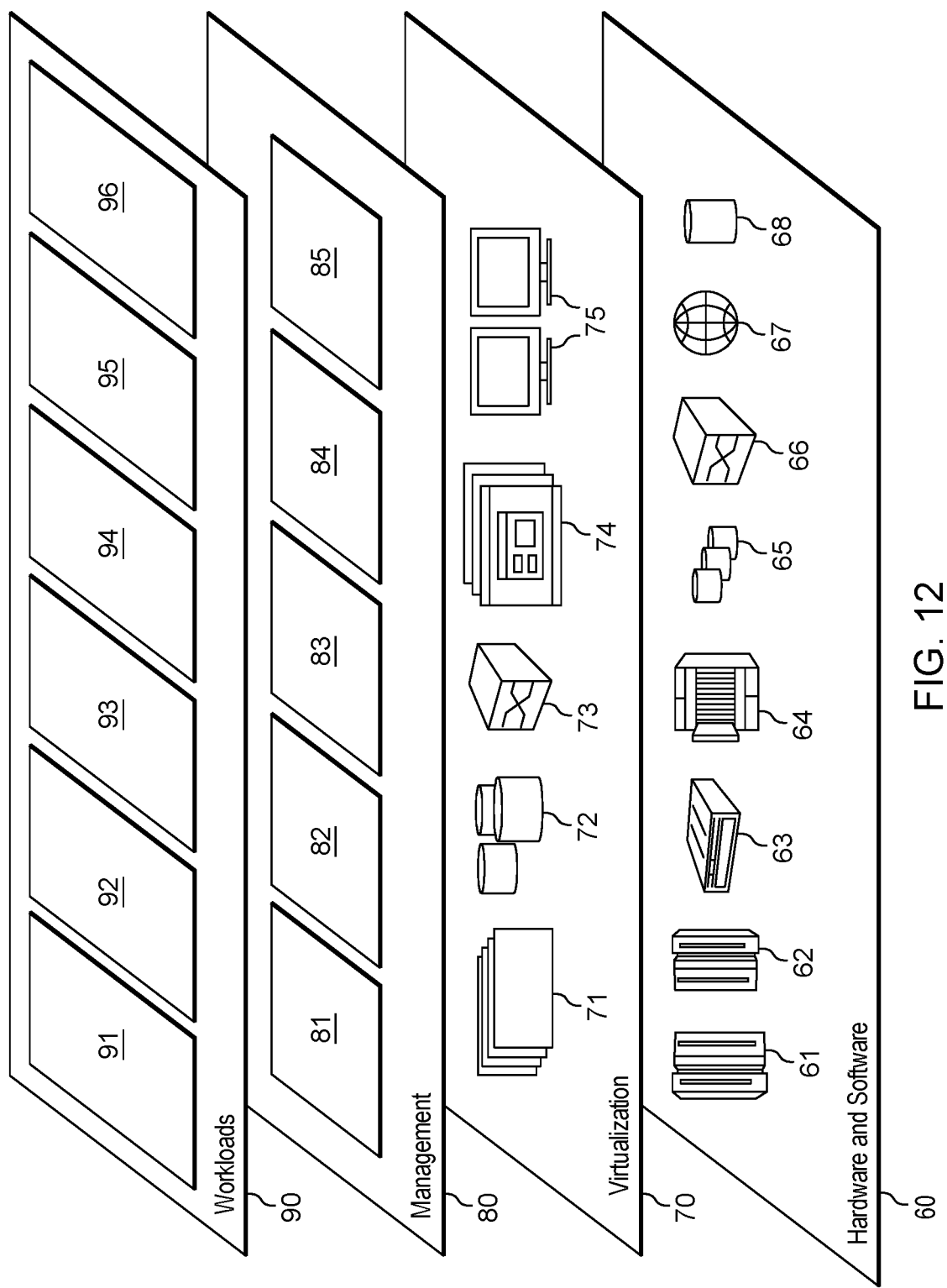
FIG. 12 depicts abstraction model layers according to an embodiment of the present invention.

FIG. 12 depicts abstraction model layers according to an embodiment of the present invention. Referring now to FIG. 12, a set of functional abstraction layers provided by cloud computing environment 50 (FIG. 11) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and engagement communicative strategy determination 96.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for outputting an engagement communicative strategy, the method comprising:
   receiving, by a processor, a patient authored text corpus from a data source external to the processor, wherein the patient authored text corpus is structured text data;
   receiving, by the processor, patient authored health data;
   training, by the processor, a communicative model based on the patient authored text corpus;
   generating, by the processor, a set of patient profiles based on the patient authored text corpus and the patient authored health data;
   constructing, by the processor, a knowledge based system based on the communicative model and the set of patient profiles, wherein the knowledge based system includes an inference engine and a knowledge base, the inference engine including a set of inference rules executable by the processor to infer facts in the knowledge base, wherein constructing the knowledge based system includes populating the knowledge base with outcomes determined by the communicative model, the knowledge base is represented as an ontology including a set of objects representing the facts in the knowledge base, and each object includes one or more pointers that point to another object among the knowledge base;
   deploying, by the processor, the knowledge based system to a device implementing an interactive application;
   receiving, by the processor from the device implementing the interactive application, a request for an engagement communicative strategy associated with an entity, the request being inputted by a user of the device;
   retrieving, by the processor, a patient profile of the entity from the set of patient profiles;
   inputting, by the processor, the patient profile, an engagement degree, and an engagement score to the knowledge based system, wherein the engagement degree is representative of a level of engagement of the entity in a patient engagement process, and the engagement score is representative of an effectiveness of a strategy to improve the level of engagement of the entity in the patient engagement process;
   executing, by the processor, the inference engine of the knowledge based system to infer facts in the knowledge base relating to the engagement communicative strategy associated with the entity based on the patient profile, the engagement degree, and the engagement score; and
   outputting, by the processor, the engagement communicative strategy to the device implementing the interactive application, wherein the engagement communicative strategy specifies a communication scheme for the user to communicate with the entity.

2. The method of claim 1, further comprising:
   executing, by the processor, a set of executable code stored in a memory to perform:
      selecting, based on selection criteria indicated by the set of instructions, a particular health behavior change model from a plurality of health behavior change models stored in the memory;
      identifying, according to the set of instructions stored in the memory, a communication taxonomy among a plurality of communication taxonomies;
      annotating, by the processor, the patient authored text corpus based on the particular health behavior model and the identified communicative taxonomy to generate annotated text data; and
      performing a supervised machine learning technique to train the communicative model using the annotated text data as training data.

3. The method of claim 1, further comprising:
   determining, by the processor, whether the patient authored text corpus is received for the first time;
   in response to the patient authored text corpus being received for the first time:
      annotating, by the processor, the patient authored text corpus based on a health behavior model and a communicative taxonomy to generate annotated text data;
      storing, by the processor, the annotated text data in a knowledge database;
   in response to the patient authored text corpus not being received for the first time:
      retrieving, by the processor, the annotated text data from the knowledge database;

wherein training the communicative model includes training the communicative model using the annotated text data.

4. The method of claim 1, further comprising:
receiving, by the processor, new patient authored text corpus;
receiving, by the processor, new patient authored health data;
retraining, by the processor, the communicative model based on the new patient authored text corpus;
updating, by the processor, the set of patient profiles based on the new patient authored text corpus and the new patient authored health data; and
updating, by the processor, the knowledge based system using the retrained communicative model and the updated patient profiles.

5. The method of claim 1, wherein the engagement communicative strategy further specifies at least one of:
the patient profile;
the current engagement stage;
a next engagement stage;
the engagement degree; and
the engagement score, wherein the communication scheme includes a suggestion of strategies for achieving the next engagement stage.

6. The method of claim 1, further comprising:
receiving, by the processor, a request for an engagement communicative strategy associated with a population;
retrieving, by the processor, a subset of patient profiles among the set of patient profiles, wherein the subset of patient profiles is associated with entities among the population;
inputting, by the processor, the subset of patient profiles, a set of engagement degree associated with the population, and a set of engagement scores associated with the population, to the knowledge based system;
executing, by the processor, the knowledge based system to determine an engagement communicative strategy associated with the population; and
outputting, by the processor, the engagement communicative strategy associated with the population, wherein the engagement communicative strategy specifies a communication scheme to communicate with the entities among the population.

7. The method of claim 6, wherein the communication scheme to communicate with the entities among the population includes a suggestion to prioritize communication with particular entities among the population.

8. A system comprising:
a memory configured to store a set of engagement instructions;
a processor configured to be in communication with the memory, the processor being configured to execute the set of engagement instructions stored in the memory to:
receive a patient authored text corpus from a data source external to the processor, wherein the patient authored text corpus is structured text data;
receive patient authored health data;
train a communicative model based on the patient authored text corpus;
generate a set of patient profiles based on the patient authored text corpus and the patient authored health data;
construct a knowledge based system based on the communicative model and the set of patient profiles, wherein the construction of the knowledge based system includes populating the knowledge base with outcomes determined by the communicative model, the knowledge based system includes an inference engine and a knowledge base, the inference engine including a set of inference rules executable by the processor to infer facts in the knowledge base, wherein the knowledge base is represented as an ontology including a set of objects representing the facts in the knowledge base, and each object includes one or more pointers that point to another object among the knowledge base;
deploy the knowledge based system to a device implementing an interactive application;
receive, from the device implementing the interactive application, a request for an engagement communicative strategy associated with an entity, the request being inputted by a user of the device;
retrieve a patient profile of the entity from the set of patient profiles;
input the patient profile, an engagement degree, and an engagement score to the knowledge based system, wherein the engagement degree is representative of a level of engagement of the entity in a patient engagement process, and the engagement score is representative of an effectiveness of a strategy to improve the level of engagement of the entity in the patient engagement process;
execute the inference engine of the knowledge based system to infer facts in the knowledge base relating to the engagement communicative strategy associated with the entity based on the patient profile, the engagement degree, and the engagement score; and
output the engagement communicative strategy to the device implementing the interactive application, wherein the engagement communicative strategy specifies a communication scheme for the user to communicate with the entity.

9. The system of claim 8, wherein the processor is further configured to:
execute a set of executable code stored in a memory to:
select, based on selection criteria indicated by the set of instructions, a particular health behavior change model from a plurality of health behavior change models stored in the memory;
identify, according to the set of instructions stored in the memory, a communication taxonomy among a plurality of communication taxonomies;
annotate the patient authored text corpus based on the particular health behavior model and the identified communicative taxonomy to generate annotated text data; and
perform a supervised machine learning technique to train the communicative model using the annotated text data as training data.

10. The system of claim 8, wherein the processor is further configured to:
determine whether the patient authored text corpus is received for the first time;
in response to the patient authored text corpus being received for the first time:
annotate the patient authored text corpus based on a health behavior model and a communicative taxonomy to generate annotated text data;
store in a knowledge database;
in response to the patient authored text corpus not being received for the first time:
retrieve the annotated text data from the knowledge database;

wherein training the communicative model includes training the communicative model using the annotated text data.

11. The system of claim 8, wherein the processor is further configured to:
receive new patient authored text corpus;
receive new patient authored health data;
retrain the communicative model based on the new patient authored text corpus;
update the set of patient profiles based on the new patient authored text corpus and the new patient authored health data; and
update the knowledge based system using the retrained communicative model and the updated patient profiles.

12. The system of claim 8, wherein the engagement communicative strategy further specifies at least one of:
the patient profile;
the current engagement stage;
a next engagement stage;
the engagement degree; and
the engagement score, wherein the communication scheme includes a suggestion of strategies for achieving the next engagement stage.

13. The system of claim 8, wherein the processor is further configured to:
receive a request for an engagement communicative strategy associated with a population;
retrieve a subset of patient profiles among the set of patient profiles, wherein the subset of patient profiles is associated with entities among the population;
input the subset of patient profiles, a set of engagement degree associated with the population, and a set of engagement scores associated with the population, to the knowledge based system;
execute the knowledge based system to determine an engagement communicative strategy associated with the population; and
output the engagement communicative strategy associated with the population, wherein the engagement communicative strategy specifies a communication scheme to communicate with the entities among the population.

14. The system of claim 13, wherein the communication scheme to communicate with the entities among the population includes a suggestion to prioritize communication with particular entities among the population.

15. A computer program product for outputting an engagement communicative strategy, the computer program product comprising a computer readable storage medium having program instructions embodied therewith, the program instructions executable by a processing element of a device to cause the device to:
receive a patient authored text corpus from a data source external to the processor, wherein the patient authored text corpus is structured text data;
receive patient authored health data;
train a communicative model based on the patient authored text corpus;
generate a set of patient profiles based on the patient authored text corpus and the patient authored health data;
construct a knowledge based system based on the communicative model and the set of patient profiles, wherein the construction of the knowledge based system includes populating the knowledge base with outcomes determined by the communicative model the knowledge based system includes an inference engine and a knowledge base, the inference engine including a set of inference rules executable by the processor to infer facts included in the knowledge base, wherein the knowledge base is represented as an ontology including a set of objects representing the facts in the knowledge base, and each object includes one or more pointers that point to another object among the knowledge base;
deploy the knowledge based system to a device implementing an interactive application;
receive, from the device implementing the interactive application, a request for an engagement communicative strategy associated with an entity, the request being inputted by a user of the device;
retrieve a patient profile of the entity from the set of patient profiles;
input the patient profile, an engagement degree, and an engagement score to the knowledge based system, wherein the engagement degree is representative of a level of engagement of the entity in a patient engagement process, and the engagement score is representative of an effectiveness of a strategy to improve the level of engagement of the entity in the patient engagement process;
execute the inference engine of the knowledge based system to infer facts in the knowledge base relating to the engagement communicative strategy associated with the entity based on the patient profile, the engagement degree, and the engagement score; and
output the engagement communicative strategy to the device implementing the interactive application, wherein the engagement communicative strategy specifies a communication scheme for the user to communicate with the entity.

16. The computer program product of claim 15, wherein the program instructions are further executable by the processing element of the device to cause the device to:
execute a set of executable code stored in a memory to:
select, based on selection criteria indicated by the set of instructions, a particular health behavior change model from a plurality of health behavior change models stored in the memory;
identify, according to the set of instructions stored in the memory, a communication taxonomy among a plurality of communication taxonomies;
annotate the patient authored text corpus based on the particular health behavior model and the identified communicative taxonomy to generate annotated text data; and
perform a supervised machine learning technique to train the communicative model using the annotated text data as training data.

17. The computer program product of claim 15, wherein the program instructions are further executable by the processing element of the device to cause the device to:
determine whether the patient authored text corpus is received for the first time;
in response to the patient authored text corpus being received for the first time:
annotate the patient authored text corpus based on a health behavior model and a communicative taxonomy to generate annotated text data;
store the annotated text data in a knowledge database;
in response to the patient authored text corpus not being received for the first time:
retrieve the annotated text data from the knowledge database;

wherein training the communicative model includes training the communicative model using the annotated text data.

18. The computer program product of claim 15, wherein the program instructions are further executable by the processing element of the device to cause the device to:
   receive new patient authored text corpus;
   receive new patient authored health data;
   retrain the communicative model based on the new patient authored text corpus;
   update the set of patient profiles based on the new patient authored text corpus and the new patient authored health data; and
   update the knowledge base using the retrained communicative model and the updated patient profiles.

19. The computer program product of claim 15, wherein the engagement communicative strategy further specifies at least one of:
   the patient profile;
   the current engagement stage;
   a next engagement stage;
   the engagement degree; and
   the engagement score, wherein the communication scheme includes a suggestion of strategies for achieving the next engagement stage.

20. The computer program product of claim 15, wherein the program instructions are further executable by the processing element of the device to cause the device to:
   receive a request for an engagement communicative strategy associated with a population;
   retrieve a subset of patient profiles among the set of patient profiles, wherein the subset of patient profiles is associated with entities among the population;
   input the subset of patient profiles, a set of engagement degree associated with the population, and a set of engagement scores associated with the population, to the knowledge based system;
   execute the knowledge based system to determine an engagement communicative strategy associated with the population; and
   output the engagement communicative strategy associated with the population, wherein the engagement communicative strategy specifies a communication scheme to communicate with the entities among the population.

* * * * *